US007704267B2

(12) United States Patent
Tessmer

(10) Patent No.: US 7,704,267 B2
(45) Date of Patent: Apr. 27, 2010

(54) NON-ENTANGLING VENA CAVA FILTER

(75) Inventor: Alexander W. Tessmer, Phoenix, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 506 days.

(21) Appl. No.: 10/912,601

(22) Filed: Aug. 4, 2004

(65) Prior Publication Data

US 2006/0030875 A1    Feb. 9, 2006

(51) Int. Cl.
*A61M 29/00* (2006.01)
(52) U.S. Cl. ....................................................... 606/200
(58) Field of Classification Search ................. 606/200; 128/830, 831
See application file for complete search history.

(56) References Cited

U.S. PATENT DOCUMENTS

| 3,540,431 A | 11/1970 | Mobin-Uddia |
| 3,952,747 A | 4/1976 | Kimmell, Jr. |
| 4,000,739 A | 1/1977 | Stevens |
| 4,282,876 A | 8/1981 | Flynn |
| 4,283,447 A | 8/1981 | Flynn |
| 4,411,655 A | 10/1983 | Schreck |
| 4,419,095 A | 12/1983 | Nebergau et al. |
| 4,425,908 A | 1/1984 | Simon |
| 4,494,531 A | 1/1985 | Gianturco |
| 4,586,501 A | 5/1986 | Claracq |
| 4,588,399 A | 5/1986 | Nebergall et al. |
| 4,590,938 A | 5/1986 | Segura et al. |
| 4,611,594 A | 9/1986 | Grayhack et al. |
| 4,619,246 A | 10/1986 | Molgaard-Nielsen et al. |
| 4,643,184 A * | 2/1987 | Mobin-Uddin ............... 606/200 |
| 4,657,024 A | 4/1987 | Coneys |

(Continued)

FOREIGN PATENT DOCUMENTS

EP    1 042 996 A2    10/2000

(Continued)

OTHER PUBLICATIONS

Osamu Nakajima, et al., "Massive Deep Vein Thrombosis After Cesarean Section Treated With A Temporary Inferior Vena Cava Filter: A Case Report", J Cardiol 2000; 36(5): pp. 337-342.

(Continued)

*Primary Examiner*—(Jackie) Tan-Uyen T. Ho
*Assistant Examiner*—Melanie Tyson
(74) *Attorney, Agent, or Firm*—Rutan & Tucker, LLP

(57) ABSTRACT

An implantable vessel filter device having a plurality of radially expandable legs with hooks, and a center-post configured to prevent entanglement of the radially expandable legs when they are compressed against the center-post. In one variation, the filter device includes a first set of legs, forming a first filter basket in the expanded position, and a second set of legs, forming a second filter basket distal to the first filter in the expanded position. Hooks may be provided on the second set of legs to prevent migration of the filter along the vessel after the filter is deployed. Grooves may be provided along the shaft of the center-post to receive the hooks and prevent the hooks from interlocking when the legs of the filter are compressed along the center-post.

23 Claims, 4 Drawing Sheets

U.S. PATENT DOCUMENTS

| | | |
|---|---|---|
| 4,688,553 A | 8/1987 | Metals |
| 4,710,192 A | 12/1987 | Liotta et al. |
| 4,722,344 A | 2/1988 | Cambron et al. |
| 4,727,873 A | 3/1988 | Mobin-Uddia |
| 4,781,177 A | 11/1988 | Lebigot |
| 4,793,348 A | 12/1988 | Palmaz |
| 4,798,591 A | 1/1989 | Okada |
| 4,817,600 A | 4/1989 | Herms et al. |
| 4,832,055 A * | 5/1989 | Palestrant .................... 128/899 |
| 4,838,879 A | 6/1989 | Tanabe et al. |
| 4,857,062 A | 8/1989 | Russell |
| 4,863,442 A | 9/1989 | De Mello et al. |
| 4,873,978 A | 10/1989 | Ginsburg |
| 4,886,506 A | 12/1989 | Lovgren et al. |
| 4,898,591 A | 2/1990 | Jang et al. |
| 4,922,905 A | 5/1990 | Strecker |
| 4,950,227 A | 8/1990 | Savin et al. |
| 4,957,501 A | 9/1990 | Lahille et al. |
| 4,969,891 A | 11/1990 | Gewertz |
| 4,990,156 A | 2/1991 | Lefebvre |
| 5,045,072 A | 9/1991 | Castillo et al. |
| 5,059,205 A | 10/1991 | El-Noumou et al. |
| 5,108,418 A | 4/1992 | Lefebvre |
| 5,114,408 A | 5/1992 | Fleischhaker et al. |
| 5,133,733 A | 7/1992 | Rasmussen et al. |
| 5,147,379 A * | 9/1992 | Sabbaghian et al. .......... 606/206 |
| 5,152,777 A | 10/1992 | Goldberg et al. |
| 5,171,232 A | 12/1992 | Castillo |
| 5,188,616 A | 2/1993 | Nadal |
| 5,203,776 A | 4/1993 | Durfee |
| 5,234,416 A | 8/1993 | Macaulay et al. |
| 5,234,458 A | 8/1993 | Metais |
| 5,242,462 A | 9/1993 | El-Nounou et al. |
| 5,300,086 A | 4/1994 | Gory et al. |
| 5,304,156 A | 4/1994 | Sylvanowicz et al. |
| 5,324,304 A | 6/1994 | Rasmussen |
| 5,329,942 A | 7/1994 | Gunther et al. |
| 5,350,398 A | 9/1994 | Pavenik et al. |
| 5,358,493 A | 10/1994 | Schweich, Jr. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,421,832 A | 6/1995 | Lefebvre |
| 5,423,851 A | 6/1995 | Samuels |
| 5,443,497 A | 8/1995 | Venbrux |
| 5,485,667 A | 1/1996 | Kleshinski |
| 5,531,788 A | 7/1996 | Dibie et al. |
| 5,545,151 A | 8/1996 | O'Connor |
| 5,549,576 A | 8/1996 | Patterson et al. |
| 5,558,652 A | 9/1996 | Henke |
| 5,601,568 A | 2/1997 | Chevillon et al. |
| 5,601,595 A | 2/1997 | Smith |
| 5,624,508 A | 4/1997 | Flomenblit et al. |
| 5,626,605 A | 5/1997 | Irie |
| 5,634,942 A | 6/1997 | Chevillon et al. |
| 5,641,364 A | 6/1997 | Golberg et al. |
| 5,649,906 A | 7/1997 | Gory et al. |
| 5,669,879 A | 9/1997 | Duer |
| 5,669,933 A | 9/1997 | Simon et al. |
| 5,672,153 A | 9/1997 | Lax |
| 5,672,158 A | 9/1997 | Okada et al. |
| 5,681,347 A | 10/1997 | Cathcart et al. |
| 5,683,411 A | 11/1997 | Kavteladze et al. |
| 5,695,518 A | 12/1997 | Laerum |
| 5,695,519 A | 12/1997 | Summers et al. |
| 5,702,370 A | 12/1997 | Sylvanowicz et al. |
| 5,704,910 A | 1/1998 | Humes |
| 5,704,926 A | 1/1998 | Sutton |
| 5,709,704 A | 1/1998 | Nott et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,759,192 A | 6/1998 | Saunders |
| 5,769,816 A | 6/1998 | Barbut |
| 5,776,162 A | 7/1998 | Kleshinski |
| 5,780,807 A | 7/1998 | Saunders |
| 5,800,457 A | 9/1998 | Gelbfish |
| 5,800,515 A | 9/1998 | Nadal et al. |
| 5,830,222 A | 11/1998 | Makower |
| 5,836,968 A | 11/1998 | Simon et al. |
| 5,836,969 A | 11/1998 | Kim et al. |
| 5,853,420 A | 12/1998 | Chevillon et al. |
| 5,893,869 A | 4/1999 | Barnhart et al. |
| 5,897,497 A | 4/1999 | Fernandez |
| 5,911,704 A | 6/1999 | Humes |
| 5,919,224 A | 7/1999 | Thompson et al. |
| 5,928,261 A | 7/1999 | Ruiz |
| 5,951,585 A | 9/1999 | Cathcart |
| 5,954,741 A | 9/1999 | Fox |
| 5,968,071 A | 10/1999 | Chevillon et al. |
| 5,972,019 A | 10/1999 | Engelson et al. |
| 5,976,172 A | 11/1999 | Homsma et al. |
| 5,984,947 A | 11/1999 | Smith |
| 6,001,118 A | 12/1999 | Daniel et al. |
| 6,007,558 A * | 12/1999 | Ravenscroft et al. ........ 606/200 |
| 6,013,093 A | 1/2000 | Nott et al. |
| 6,036,723 A | 3/2000 | Anidjar et al. |
| 6,051,015 A | 4/2000 | Maahs |
| 6,059,814 A | 5/2000 | Ladd |
| 6,059,825 A | 5/2000 | Hobbs et al. |
| 6,066,158 A | 5/2000 | Engelson et al. |
| 6,068,638 A | 5/2000 | Makower |
| 6,071,292 A | 6/2000 | Makower et al. |
| 6,077,880 A | 6/2000 | Castillo et al. |
| 6,080,178 A | 6/2000 | Meglin |
| 6,099,549 A | 8/2000 | Bosma et al. |
| 6,126,645 A | 10/2000 | Thompson |
| 6,126,673 A | 10/2000 | Kim et al. |
| 6,131,266 A | 10/2000 | Saunders |
| 6,132,388 A | 10/2000 | Fleming |
| 6,146,404 A | 11/2000 | Kim et al. |
| 6,156,055 A | 12/2000 | Ravenscroft |
| 6,159,225 A | 12/2000 | Makower |
| 6,162,357 A | 12/2000 | Pakki et al. |
| 6,165,179 A | 12/2000 | Cathcart |
| 6,165,200 A | 12/2000 | Tsugita et al. |
| 6,171,297 B1 | 1/2001 | Pedersen |
| 6,190,353 B1 | 2/2001 | Makower et al. |
| 6,193,739 B1 * | 2/2001 | Chevillon et al. ........... 606/200 |
| 6,193,748 B1 | 2/2001 | Thompson et al. |
| 6,214,025 B1 | 4/2001 | Thistle et al. |
| 6,217,600 B1 | 4/2001 | DiMatteo |
| 6,228,052 B1 | 5/2001 | Pohndorf |
| 6,231,581 B1 | 5/2001 | Shank et al. |
| 6,231,587 B1 | 5/2001 | Makower |
| 6,231,588 B1 | 5/2001 | Zadno-Azizi |
| 6,231,589 B1 * | 5/2001 | Wessman et al. ............ 606/200 |
| 6,235,045 B1 | 5/2001 | Barbut |
| 6,241,746 B1 | 6/2001 | Bosma et al. |
| 6,245,012 B1 | 6/2001 | Kleshinski |
| 6,251,122 B1 | 6/2001 | Tsukernik |
| 6,254,633 B1 | 7/2001 | Pinchuk et al. |
| 6,258,026 B1 * | 7/2001 | Ravenscroft et al. ........ 600/200 |
| 6,258,101 B1 | 7/2001 | Blake |
| 6,264,671 B1 | 7/2001 | Stack et al. |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,283,983 B1 | 9/2001 | Makower et al. |
| 6,287,317 B1 | 9/2001 | Makower et al. |
| 6,290,710 B1 | 9/2001 | Cryer et al. |

| | | |
|---|---|---|
| 6,302,875 B1 | 10/2001 | Makower et al. |
| 6,302,891 B1 | 10/2001 | Nadal |
| 6,322,541 B2 | 11/2001 | West et al. |
| 6,325,790 B1 | 12/2001 | Trotta |
| 6,328,755 B1 | 12/2001 | Marshall |
| 6,331,183 B1 | 12/2001 | Suon |
| 6,336,934 B1 | 1/2002 | Gilson et al. |
| 6,342,062 B1 | 1/2002 | Suon et al. |
| 6,342,063 B1 | 1/2002 | DeVries et al. |
| 6,383,193 B1 | 5/2002 | Cathcart |
| 6,383,206 B1 | 5/2002 | Gillick et al. |
| 6,391,045 B1 | 5/2002 | Kim et al. |
| 6,402,771 B1 | 6/2002 | Palmer et al. |
| 6,416,530 B2 | 7/2002 | DeVries et al. |
| 6,428,559 B1 | 8/2002 | Johnson |
| 6,432,127 B1 | 8/2002 | Kim et al. |
| 6,436,121 B1 | 8/2002 | Blom |
| 6,440,077 B1 | 8/2002 | Jung et al. |
| 6,442,413 B1 | 8/2002 | Silver |
| 6,443,971 B1 | 9/2002 | Boylan et al. |
| 6,443,972 B1 | 9/2002 | Bosma et al. |
| 6,447,530 B1 * | 9/2002 | Ostrovsky et al. ............ 606/200 |
| 6,458,145 B1 | 10/2002 | Ravenscroft et al. |
| 6,468,290 B1 | 10/2002 | Weldon et al. |
| 6,482,222 B1 | 11/2002 | Bruckheimer et al. |
| 6,485,500 B1 | 11/2002 | Kokish et al. |
| 6,485,501 B1 | 11/2002 | Green |
| 6,485,502 B2 | 11/2002 | Don Michael et al. |
| 6,488,662 B2 | 12/2002 | Sirimanne |
| 6,497,709 B1 | 12/2002 | Heath |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,503 B1 | 1/2003 | Burkett et al. |
| 6,517,559 B1 | 2/2003 | O'Connell |
| 6,517,573 B1 | 2/2003 | Pollock et al. |
| 6,537,294 B1 | 3/2003 | Boyle et al. |
| 6,537,295 B2 | 3/2003 | Petersen |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,280 B1 | 4/2003 | Daniel et al. |
| 6,551,303 B1 | 4/2003 | Van Tassel et al. |
| 6,551,340 B1 | 4/2003 | Konya et al. |
| 6,551,342 B1 | 4/2003 | Shen et al. |
| 6,558,404 B2 | 5/2003 | Tsukemik |
| 6,558,405 B1 | 5/2003 | McInnes |
| 6,558,406 B2 | 5/2003 | Okada |
| 6,563,080 B2 | 5/2003 | Shapovalov et al. |
| 6,569,183 B1 | 5/2003 | Kim et al. |
| 6,569,184 B2 | 5/2003 | Huter |
| 6,572,605 B1 | 6/2003 | Humes |
| 6,575,997 B1 | 6/2003 | Palmer et al. |
| 6,582,447 B1 | 6/2003 | Patel et al. |
| 6,589,266 B2 | 7/2003 | Whitcher et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,602,273 B2 | 8/2003 | Marhall |
| 6,607,553 B1 | 8/2003 | Healy et al. |
| 6,610,077 B1 | 8/2003 | Hancock et al. |
| 6,616,680 B1 | 9/2003 | Thielen |
| 6,616,681 B2 | 9/2003 | Hanson et al. |
| 6,620,183 B2 | 9/2003 | DiMatteo |
| 6,623,450 B1 | 9/2003 | Dutta |
| 6,623,506 B2 | 9/2003 | McGuckin, Jr. et al. |
| 6,629,993 B2 | 10/2003 | Voinov |
| 6,640,077 B2 | 10/2003 | Suzuki |
| 6,641,590 B1 | 11/2003 | Palmer et al. |
| 6,645,152 B1 | 11/2003 | Jung et al. |
| 6,645,224 B2 | 11/2003 | Gilson et al. |
| 6,652,555 B1 | 11/2003 | Van Tassel et al. |
| 6,652,556 B1 | 11/2003 | Van Tassel et al. |
| 6,652,558 B2 | 11/2003 | Patel et al. |
| 6,652,692 B2 | 11/2003 | Pedersen |
| 6,656,203 B2 | 12/2003 | Roth et al. |
| 6,660,021 B1 | 12/2003 | Palmer et al. |
| 6,663,650 B2 | 12/2003 | Sepetka et al. |
| 6,679,902 B1 | 1/2004 | Boyle et al. |
| 6,679,903 B2 | 1/2004 | Kurz |
| 6,685,722 B1 | 2/2004 | Rosenbluth et al. |
| 6,685,738 B2 | 2/2004 | Chouinard et al. |
| 6,689,150 B1 | 2/2004 | Van Tassel et al. |
| 6,695,813 B1 | 2/2004 | Boyle et al. |
| 6,696,667 B1 | 2/2004 | Flanagan |
| 6,702,834 B1 | 3/2004 | Boylan et al. |
| 6,706,054 B2 | 3/2004 | Wessman et al. |
| 6,716,208 B2 | 4/2004 | Humes |
| 6,719,717 B1 | 4/2004 | Johnson et al. |
| 6,719,772 B2 | 4/2004 | Trask et al. |
| 6,726,621 B2 | 4/2004 | Suon |
| 6,730,108 B2 | 5/2004 | Van Tassel et al. |
| 6,736,842 B2 | 5/2004 | Healy et al. |
| 6,755,846 B1 | 6/2004 | Yadav |
| 6,761,732 B2 | 7/2004 | Burkett et al. |
| 6,773,448 B2 | 8/2004 | Kusleika et al. |
| 6,776,770 B1 | 8/2004 | Trerotola |
| 6,776,774 B2 | 8/2004 | Tansey, Jr. et al. |
| 6,783,538 B2 | 8/2004 | McGuckin, Jr. et al. |
| 6,792,979 B2 | 9/2004 | Konya et al. |
| 6,793,665 B2 | 9/2004 | McGuckin, Jr. et al. |
| 6,818,006 B2 | 11/2004 | Douk et al. |
| 6,840,950 B2 | 1/2005 | Stanford et al. |
| 6,843,798 B2 | 1/2005 | Kusleika et al. |
| 6,849,061 B2 | 2/2005 | Wagner |
| 6,872,217 B2 | 3/2005 | Walak et al. |
| 6,881,218 B2 | 4/2005 | Beyer et al. |
| 7,001,424 B2 | 2/2006 | Patel et al. |
| 7,033,376 B2 | 4/2006 | Tsukernik |
| 7,041,117 B2 | 5/2006 | Suon et al. |
| 7,147,649 B2 | 12/2006 | Thomas |
| 7,314,477 B1 | 1/2008 | Ravenscroft et al. |
| 7,323,003 B2 | 1/2008 | Lowe |
| 7,544,202 B2 * | 6/2009 | Cartier et al. ................ 606/200 |
| 2001/0000799 A1 | 5/2001 | Wessman et al. |
| 2001/0020175 A1 | 9/2001 | Yassour et al. |
| 2001/0023358 A1 | 9/2001 | Tsukernik |
| 2001/0039431 A1 | 11/2001 | DeVries et al. |
| 2002/0032461 A1 | 3/2002 | Marshall |
| 2002/0042626 A1 | 4/2002 | Hanson et al. |
| 2002/0045918 A1 | 4/2002 | Suon et al. |
| 2002/0055767 A1 | 5/2002 | Forde et al. |
| 2002/0116024 A1 | 8/2002 | Goldberg et al. |
| 2002/0138097 A1 | 9/2002 | Ostrovsky et al. |
| 2002/0193825 A1 | 12/2002 | McGuckin, Jr. et al. |
| 2002/0193826 A1 | 12/2002 | McGuckin, Jr. et al. |
| 2002/0193827 A1 | 12/2002 | McGuckin, Jr. et al. |
| 2002/0193828 A1 | 12/2002 | Griffin et al. |
| 2003/0004540 A1 | 1/2003 | Linder et al. |
| 2003/0004541 A1 | 1/2003 | Linder et al. |
| 2003/0028241 A1 | 2/2003 | Stinson |
| 2003/0071285 A1 | 4/2003 | Tsukernik |
| 2003/0093110 A1 | 5/2003 | Vale |
| 2003/0097145 A1 | 5/2003 | Goldberg et al. |
| 2003/0109824 A1 | 6/2003 | Anderson et al. |
| 2003/0109897 A1 | 6/2003 | Walak et al. |
| 2003/0114735 A1 | 6/2003 | Silver et al. |
| 2003/0114880 A1 * | 6/2003 | Hansen et al. ............. 606/200 |
| 2003/0130680 A1 | 7/2003 | Russell |
| 2003/0139765 A1 | 7/2003 | Patel et al. |
| 2003/0153945 A1 | 8/2003 | Patel et al. |
| 2003/0163159 A1 | 8/2003 | Patel et al. |
| 2003/0171771 A1 | 9/2003 | Anderson et al. |
| 2003/0176888 A1 | 9/2003 | O'Connell |
| 2003/0191516 A1 | 10/2003 | Weldon et al. |
| 2003/0195554 A1 | 10/2003 | Shen et al. |

| | | |
|---|---|---|
| 2003/0195556 A1 | 10/2003 | Stack et al. |
| 2003/0199918 A1 | 10/2003 | Patel et al. |
| 2003/0208227 A1 | 11/2003 | Thomas |
| 2003/0208253 A1 | 11/2003 | Beyer et al. |
| 2004/0006364 A1 | 1/2004 | Ladd |
| 2004/0059373 A1 | 3/2004 | Shapiro et al. |
| 2004/0068288 A1 | 4/2004 | Palmer |
| 2004/0073252 A1 | 4/2004 | Goldberg et al. |
| 2004/0082966 A1 | 4/2004 | WasDyke |
| 2004/0087999 A1 | 5/2004 | Bosma et al. |
| 2004/0088000 A1 | 5/2004 | Muller |
| 2004/0088001 A1 | 5/2004 | Bosma et al. |
| 2004/0088002 A1 | 5/2004 | Boyle et al. |
| 2004/0093015 A1 | 5/2004 | Ogle |
| 2004/0116959 A1 | 6/2004 | McGuckin, Jr. et al. |
| 2004/0138693 A1 | 7/2004 | Eskuri et al. |
| 2004/0153110 A1 | 8/2004 | Kurz et al. |
| 2004/0153118 A1 | 8/2004 | Clubb et al. |
| 2004/0153119 A1 | 8/2004 | Kusleika et al. |
| 2004/0158273 A1 | 8/2004 | Weaver et al. |
| 2004/0158274 A1 | 8/2004 | WasDyke |
| 2004/0167568 A1 | 8/2004 | Boyle et al. |
| 2004/0172042 A1 | 9/2004 | Suon et al. |
| 2004/0176672 A1 | 9/2004 | Silver et al. |
| 2004/0186510 A1 | 9/2004 | Weaver |
| 2004/0186512 A1 | 9/2004 | Bruckheimer et al. |
| 2004/0193209 A1 | 9/2004 | Pavenik et al. |
| 2004/0199240 A1 | 10/2004 | Dorn |
| 2004/0220610 A1 | 11/2004 | Kreidler et al. |
| 2004/0220611 A1 | 11/2004 | Ogle |
| 2004/0230220 A1 | 11/2004 | Osborne |
| 2004/0243173 A1 | 12/2004 | Inoue |
| 2005/0015111 A1 | 1/2005 | McGuckin, Jr. et al. |
| 2005/0019370 A1 | 1/2005 | Humes |
| 2005/0021075 A1 | 1/2005 | Bonnette et al. |
| 2005/0021076 A1 | 1/2005 | Mazzocchi et al. |
| 2005/0021152 A1 | 1/2005 | Ogle et al. |
| 2005/0027314 A1 | 2/2005 | WasDyke |
| 2005/0055045 A1 | 3/2005 | DeVries et al. |
| 2005/0055046 A1 | 3/2005 | McGuckin, Jr. et al. |
| 2005/0080447 A1 | 4/2005 | McGuckin, Jr. et al. |
| 2005/0080449 A1 | 4/2005 | Mulder |
| 2005/0085847 A1 | 4/2005 | Galdonik et al. |
| 2005/0090858 A1 | 4/2005 | Pavlovic |
| 2005/0115111 A1 | 6/2005 | Yamashita et al. |
| 2005/0131451 A1 | 6/2005 | Kleshinski et al. |
| 2005/0159771 A1 | 7/2005 | Petersen |
| 2005/0182439 A1 | 8/2005 | Lowe |
| 2005/0222604 A1 | 10/2005 | Schaeffer |
| 2005/0288703 A1 | 12/2005 | Beyer et al. |
| 2005/0288704 A1 | 12/2005 | Cartier et al. |
| 2006/0004402 A1 | 1/2006 | Voeller et al. |
| 2006/0015137 A1 | 1/2006 | WasDyke et al. |
| 2006/0036279 A1 | 2/2006 | Eidenschink et al. |
| 2006/0041271 A1 | 2/2006 | Bosma et al. |
| 2006/0069405 A1 | 3/2006 | Schaeffer et al. |
| 2006/0069406 A1 | 3/2006 | Hendriksen et al. |
| 2006/0079928 A1 | 4/2006 | Cartier et al. |
| 2006/0079930 A1 | 4/2006 | McGuckin, Jr. et al. |
| 2006/0095068 A1 | 5/2006 | WasDyke et al. |
| 2006/0203769 A1 | 9/2006 | Saholt et al. |
| 2006/0206138 A1 | 9/2006 | Eidenschink |
| 2006/0259067 A1 | 11/2006 | Welch et al. |
| 2006/0259068 A1 | 11/2006 | Eidenschink |
| 2007/0005095 A1 | 1/2007 | Osborne et al. |
| 2007/0005104 A1 | 1/2007 | Kusleika et al. |
| 2007/0005105 A1 | 1/2007 | Kusleika et al. |

FOREIGN PATENT DOCUMENTS

| | | |
|---|---|---|
| EP | 1 092 401 A1 | 4/2001 |
| EP | 1 336 393 A2 | 8/2003 |
| EP | 1 475 110 A1 | 11/2004 |
| FR | 2 781 143 A1 | 1/2000 |
| FR | 2 791 551 A1 | 10/2000 |
| WO | WO-97/29794 A1 | 8/1997 |
| WO | WO-00/56390 A1 | 9/2000 |
| WO | WO-02/055125 A2 | 7/2002 |
| WO | WO-03/003927 A1 | 1/2003 |
| WO | WO-03/004074 A3 | 1/2003 |
| WO | WO-2004/012587 A2 | 2/2004 |
| WO | WO-2005/009214 A2 | 2/2005 |

OTHER PUBLICATIONS

J. Neuerburg et al, "New Retrievable Percutaneous Vena Cava Filter: Experimental In Vitro and In Vitro Evaluation", Cardiovasc Intervent Radiol, 1993, 16:224-229.

J.M. Neuerburg, et al., "Percutaneous Retrieval of the Tulip Vena Cava Filter: Feasibility, Short-and Long-Term Changes-An Experimental Study in Dogs", Cardiovascular and Interventional Radiology, 2001, 24:418-423.

O. A. Terhaar, et al., "Extended Interval For Retrieval of Gunther Tulip Filters", J Vasc Interv Radiol, Nov. 2004, 15:1257-1262.

J. Neuerburg, et al., "Developments In Inferior Vena Cava Filters", Seminars In Interventional Radiology, vol. II, No. 4, Dec. 1994, pp. 349-357.

A. M. Palestrant, et al., "Comparative In Vitro Evaluation of The Nitinol Inferior Vena Cava Filter", Radiology, Nov. 1982, 145:351-355.

P.A. Poletti, et al., "Long-Term Results of The Simon Nitinol Inferior Vena Cava Filter", Eur. Radiol, 1998, vol. 8, pp. 289-294.

D. Putterman, et al., "Aortic Pseudoaneurysm After Penetration By A Dion Nitinol Inferior Vena Cava Filter", J Vasc Interv Radiol, 2005, 16:535-538.

Z. Qian et al., "In Vitro and In Vivo Experimental Evaluation of a New Vena Cava Filter", Journal of Vascular and Interventional Radiology, May-Jun. 1994, pp. 513-518.

C.E. Ray Jr., et al., "Complications of Inferior Vena Cava Filters", Abdominal Imaging, 1996, 21:368-374.

S. Raghavan et al., "Migration of Inferior Vena Cava Filter Into Renal Hilum", Nephron, Jun. 2002; 91,2; Health & Medical Complete; p. 333.

J.O.F. Roehm Jr., "The Bird's Nest Filter: A New Percutaneous Transcatheter Inferior Vena Cava Filter", Journal of Vascular Surgery, Oct. 1984, vol. 1, No. 3.

J.O.F. Roehm Jr., et al., "The Bird's Nest Inferior Vena Cava Filter: Progress Report", Radiology, Sep. 1988, 168:745-749.

M. A. Savin et al., "Placement of Vena Cava Filters: Factors Affecting Technical Success and Immediate Complications", AJR, Sep. 2002, Vo. 179, pp. 597-602.

F. B. Rogers et al., "Five-Year Follow-Up of Prophylactic Vena Cava Filters in High-Risk Trauma Patients", Archives of Surgery, Apr. 1998, vol. 133, 4:Health & Medical Complete, p. 406.

J.-M. Schleich, et al., "Long-Term Follow-up of Percutaneous Vena Cava Filters: A Prospective Study in 100 Consecutive Patients", Eur J Vasc Endovasc Surg, 2001, vol. 21, pp. 450-457.

M. Shahmanesh et al., "Inferior Vena Cava Filters for HIV Infected Patients With Pulmonary Embolism And Contraindications to Anticoagulation", Sex Transm Inf, 2000, 76:395-397.

H. Rousseau, et al., "The 6-F Nitinol TrapEase Inferior Vena Cava Filter: Results of a Prospective Multicenter Trial", J Vasc Interv Radiol, 2001, 12:299-304.

G. W. Stoneham et al., "Temporary Inferior Vena Cava Filters: In Vitro Comparison With Permanent IVC Filters", Journal of Vascular and Interventional Radiology, Sep.-Oct. 1995, vol. 6, pp. 731-736.

R.F. Sing, "Safety and Accuracy of Bedside Carbon Dioxide Cavography For Insertion of Inferior Vena Cava Filters In The Intensive Care Unit", American College of Surgeons, Feb. 2, 2001, vol. 192, pp. 168-171.

M. Simon et al., "Simon Nitinol Inferior Vena Cava Filter: Initial Clinical Experience", Radiology, vol. 172, No. 1, pp. 99-103, Jul. 1989.

L.D. Spence et al., "Acute Upper Extremity Deep Venous Thrombosis, Safety and Effectiveness of Superior Vena Caval Filters", Radiology, Jan. 1999, vol. 210, pp. 53-58.

R.L. Leask et al., "In Vito Hemodynamic Evaluation of a Simon Nitinol Vena Cava Filter: Possible Explanation of IVC Occlusion", J Vas Interv Radiol, May 2001, 12:613-618.

F. Stosslein et al., "A Rare Complication With An Antheor Vena Cava Filter", Cardiovascular and Interventional Radiology, , 1998, 21:165-167.

M.B. Streiff, "Vena Caval Filters: A Comprehensive Review", Blood, Jun. 15, 2000, vol. 95, No. 12, pp. 3669-3677.

K. Tay et al, "Repeated Gunther Tulip Inferior Vena Cava Filter Repositioning to Prolong Implantation Time", J Vasc Interv Radiol, May 2002, 13:509-512.

F. C. Taylor et al., "Vena Tech Vena Cava Filter: Experience and Early Follow-up", Journal of Vascular Interventional Radiology, Nov. 1991, 2:435-440.

C. Thery et al., "Use of a New Removable Vena Cava Filter in Order to Prevent Pulmonary Embolism in Patients Submitted to Thrombolysis", European Heart Journal, 1990, vol. 11, 334-341.

M. Porcellini et al., "Intracardiac Migration of Nitinol TrapEase Vena Cava Filter And Paradoxical Embolism", European Journal of Cardio-Thoracic Surgery , vol. 22, 2002, pp. 460-461.

L. D. Vos et al., "The Gunther Temporary Inferior Vena Cava Filter For Short-Term Protection Against Pulmonary Embolism", Cardiovascular and Interventional Radiology, 1997, 20:91-97.

S. Watanabe et al., "Clinical Experience With Temporary Vena Cava Filters", Vascular Surgery, vol. 35, No. 4, 2001, pp. 285-291.

M. Zwaan et al., "Clinical Experience With Temporary Vena Caval Filters", JVIR, Jul.-Aug. 1998, vol. 9, No. 4, pp. 594-601.

A. Dardik et al., "Vena Cava Filter Ensnarement and Delayed Migration: An Unusual Series of Cases", Journal of Vascular Surgery, Nov. 1997, vol. 26, No. 5.

J. M. Pereira de Godoy et al., "In-Vitro Evaluation of a New Inferior Vena Cava Filter-The Stent-Filter", Vascular and Endovascular Surgery, Nov. 3, 2004, vol. 38, pp. 225-228.

B. D. Davison et al., "TrapEase Inferior Vena Cava Filter Placed Via The Basilic Arm Vein: A New Antecubital Access", J Vasc Interv Radiol, Jan. 2002, 13:107-109.

M. A. De Gregorio et al, "Retrievability of Uncoated Versus Paclitaxel-Coated Gunther-Tulip IVC Filters in an Animal Model", J Vasc Interv Radiol, Jul. 2004, 15:719-726.

M.A. de Gregorio, "Inferior Vena Cava Filter Update", Arch Bronconeumol, 2004, vol. 40, No. 5, pp. 193-195.

M.A. de Gregorio et al., "The Gunther Tulip Retrievable Filter: Prolonged Temporary Filtration by Repositioning Within the Inferior Vena Cava", J Vasc Interv Radiol, Oct. 2003, 14:1259-1265.

J.L. Ebaugh et al., "Bedside Vena Cava Filter Placement Guided With Intravascular Ultrasound", Journal of Vascular Surgery, Jul. 2001, 34:21-26.

L. J. Greenfield et al., "A New Intracaval Filter Permitting Continued Flow And Resolution of Emboli", Surgery, Apr. 1973, vol. 73, No. 4, pp. 599-606.

R. W. Gunther et al., "Vena Caval Filter to Prevent Pulmonary Embolism: Experimental Study", Radiology, Aug. 1985, 156:315-320.

A. C. Venbrux, "Protection Against Pulmonary Embolism: Permanent and Temporary Caval Filters", Associate Professor of Radiology and Surgery, Department of Radiology—CVDL, The Johns Hopkins Medical Institutions, Baltimore, MD.

J.S. Gosin et al., "Efficacy of Prophylactic Vena Cava Filters in High-Risk Trauma Patients", Ann Vasc Surg, 1997, 11:100-105.

P. Haage et al., "Prototype Percutaneous Thrombolytic Device: Preclinical Testing in Subacute Inferior Vena Caval Thrombosis in a Pig Model", Radiology, Jul. 2001, 220:135-141.

W. F. Oppat et al., "Intravascular Ultrasound-Guided Vena Cava Filter Placement" J Endovasc Surg, 1999, 6:285-287.

F.D. Hammer et al., "In Vitro Evaluation of Vena Cava Filters", Journal of Vascular and Interventional Radiology, Nov.-Dec. 1994, 5:869-876.

S.J. Savader, Inferior Vena Cava Filters, Chapter 28, pp. 367-399.

S.C. Rose et al., "Placement of Inferior Vena Caval Filters in the Intensive Care Unit", Journal of Vascular Interventional Radiology, Jan.-Feb. 1997, 8:61-64.

D. H. Epstein et al., "Experience With The Amplatz Retrievable Vena Cava Filter", Radiology, 1989, 172:105-110.

C.A. Athanasoulis et al., "Inferior Vena Caval Filters: Review of a 26-Year Single-Center Clinical Experience", Radiology, 2000, 216:54-66.

F. Fobbe et al., "Gunther Vena Caval Filter: Results of Long-Term Follow-Up", AJR, Nov. 1988, 151:1031-1034.

L.J. Greenfield et al ., "Extended Evaluation of the Titanium Greenfield Vena Caval Filter", Journal of Vascular Surgery, Nov. 1994, vol. 20, No. 3, pp. 458-465.

L. J. Greenfield et al., "Vena Caval Filter Use in Patients With Sepsis", Archives of surgery, Nov. 2003, vol. 138, No. 11, Health & Medical Complete, p. 1245.

L.J. Greenfield et al., "Suprarental Filter Placement", Journal of Vascular Surgery, Sep. 1998, 28:432-438.

L.J. Greenfield et al., "Clinical Experience With the Kim-Ray Greenfield* Vena Caval Filter", ANN SURG, Jun. 1977, vol. 185, No. 6, pp. 692-698.

C. Nutting et al., "Use of a TrapEase Device as a Temporary Caval Filter", Journal of Vascular Interventional Radiology, Aug. 2001, 12:991-993.

D. Pavcnik et al., "Retrievable IVC Square Stent Filter: Experimental Study", Cardiovascular Interventional Radiology, 1999, 22:239-245.

M. Ponchon et al., "Temporary Vena Caval Filtration Preliminary Clinical Experience With Removable Vena Caval Filters", ACTA Clinica Belgica, 1999, vol. 54, pp. 223-228.

J.A. Reekers, "Re Current Practice of Temporary Vena Cava Filter Insertion: A Multicenter Registry", Journal of Vascular Interventional Radiology, Nov.-Dec. 2000,.p. 1363.

J.A. Reekers et al., "Evaluation of The Retrievability of The OptEase IVC Filter in an Animal Model", Journal of Vascular Interventional Radiology, Mar. 2003, 15:261-267.

R.A. Reed, "The Use of Inferior Vena Cava Filters in Pediatric Patients for Pulmonary Embolus Prophylaxis", Cardiovascular and Interventional Radiology, 1996, 19:401-405.

J. B. Ricco et al., "Percutaneous Transvenous Caval Interruption with the LGM Filter", Ann Vasc Surg, 1988, 3:242-247.

J.D. Robinson et al., "In Vitro Evaluation of Caval Filters", Cardiovascular A ND Interventional Radiology, 1988, 11:346-351.

M.J. Wallace et al., "Inferior Vena Caval Stent Filter", AJR, Dec. 1986, 147:1247-1250.

K. Yavuz et al., "Retrievable of a Malpositioned Vena Cava Filter With Embolic Protection With Use of a Second Filter", Journal of Vascular Interventional Radiology, 2005, 16:531-534.

D. Danikas et al., "Use of a Fogarty Catheter to Open an Incompletely Expanded Vena Tech-LGM Vena Cava Filter", Angiology, Apr. 2001, vol. 52, No. 4, p. 283.

Adye, B. A., "Case Report: Errant Percutaneous Greenfield Filter Placement Into The Retropentoneum", Journal of Vascular Surgery, Jul. 1990, vol. 12, No. 1.

Aklog, L. et al., "Acute Pulmonary Embolectomy", Circulation, 2002, 105:1416-1419.

Alexander, J. J. et al., "Is the Increasing Use of Prophylactic Percutaneous IVC Filters Justified?", The American Journal of Surgery, Aug. 1994, vol. 168, pp. 102-106.

Andrews, R. T. et al., "Entrapment of J-Tip Guidewires by Venatech and Stainless-Steel Greenfield Vena Cava Filters During Central Venous Catheter Placement: Percutaneous Management in Four Patients", Correspondence to R.T. Andrews, M.D., The dotter Interventional Institute, Oregon Heal Sciences University, Portland, OR, pp. 424-427.

Arjomand, H. et al., "Right Ventricular Foreign Body: Percutaneous Transvenous Retrieval of a Greenfield Filter From The Right Ventricle", Angiology, 2003, vol. 54, No. 1, pp. 109-113.

Ascer, E. et al., "Superior Vena Caval Greenfield Filters: Indications, Techniques, and Results", Journal of Vascular Surgery, Mar. 1996, vol. 23, No. 3.

Asch, M. R., "Initial Experience in Humans With a New Retrievable Inferior Vena Cava Filter", Radiology, 2002, 225:835-844.

Ascher, E. et al., "Lessons Learned From a 6-Year Clinical Experience With Superior Vena Cava Greenfield Filters", Journal of Vascular Surgery, Nov. 2000, 32:881-887.

Ashley, D.W. et al., "Accurate Deployment of Vena Cava Fitters: Comparison of Intravascular Ultrasound and Contrast Venography", The Journal of Trauma Injury, Infection, and Critical Care, Jun. 2001, vol. 50, No. 6, pp. 975-981.

Aswad, M. A. et al., "Early Duplex Scan Evaluation of Four Venal Interruption Devices", Journal of Vascular Surgery, 1996, 24:809-818.

Athanasoulis, C.A. et al., "Inferior Venal Caval Filters: Review of a 26-Year Single-Center Clinical Experience", Radiology, 2000, 216:54-66.

Avery, M. et al., "Reverse Engineering of Nitinol Vena Cava Filters", Material Science 102 Semester Project, Nov. 21, 2000.

Baker, R. J., "Treatment Considerations For Inherited Thrombophilia And Pulmonary Embolus", Archives of Surgery, Feb. 2001, 136,2:237.

Balshi, J. D. et al., "Original Articles" Complications of Caval Interruption by Greenfield Filter in Quadriplegics, Journal of Vascular Surgery, Apr. 1989, vol. 9, No. 4.

Barraco, R. D. et al., "Dislodgment of Inferior Vena Cava Filters During Central Line Placement: Case Report", The Journal of Trauma, Injury, Infection and Critical Care, 2000, vol. 48, No. 1, pp. 140-142.

Barreras, J. R. et al., "Recurrent Pulmonary Embolism Despite The Use of a Greenfield Filter", Clinical Nuclear, Dec. 2001, vol. 26, No. 12, pp. 1040-1041.

Barton, A. L. et al., "Caval Filter Placement For Pulmonary Embolism in a Patient With a Deep Vein Thrombosis and Primary Intracerebral Haemorrhage", Age and Ageing, Mar. 2002, 31,2:144-146.

Becker, D. M. et al., "Inferior Vena Cava Filters", Archives of Internal Medicine, Oct. 1992, vol. 152, pp. 1985-1994.

Benjamin, M. E. et al., Duplex Ultrasound Insertion of Inferior Vena Cava Filters in Multitrauma Patients: American Journal of Surgery, Aug. 1999, vol. 178, pp. 92-97.

Binkert, C. A. et al., "Inferior Vena Cava Filter Removal After 317-Day Implantation", Journal of Vascular Radiology, Mar. 2005, 16:393-398.

Bjarnason, H. et al., "In Vitro Metal Fatigue Testing of Inferior Vena Cava Filters", Investigative Radiology, 1994, vol. 29, No. 9, pp. 817-821.

Blebea J. et al., "Deep Venous Thrombosis After Percutaneous Insertion of Vena Caval Filters", Journal of Vascular Surgery, Nov. 1999, 30:821:829.

Bochenek, K. M. et al., "Right Atrial Migration and Percutaneous Retrieval of a Gunther Tulip Inferior Vena Cava Filter", Journal of Vascular Interventional Radiology, Sep. 2003, 14:1207-1209.

Bochicchio, G. V. et al., "Acute Caval Perforation by an Inferior Vena Cava Filter in a Multitrauma Patient: Hemostatic Control With a New Surgical Hemostat", The Journal of Trauma Injury, Infection and Critical Care, 2001, 51:991-993.

Bracale, G. et al., "Spontaneous Rupture of The Iliac Vein", The Journal of Cardiovascular Surgery, 1999, 40:871-875.

Bravo, S. M. et al., "Percutaneous Venous Interventions", Vascular Medicine, 1998, 3:61-66.

Brountzos, E. N. et al., "A New Optional Vena Cava Filter: Retrieval at 12 Weeks in an Animal Model", Journal of Vascular and Interventional Radiology, Jun. 2003, 14:763-772.

Brown, D. R. et al., "Gadolinium, Carbon Dioxide, and Iodinated Contrast Material For Planning Inferior Vena Cava Filter Placement: a Prospective Trial", Journal of Vascular and Interventional Radiology, Aug. 2003, 14:1017-1022.

Browne, R. J. et al., "Guidewire Entrapment During Greenfield Filter Deployment", Journal of Vascular Surgery, Jan. 1998, 27:174-176.

Bruckheimer, E. et al., "In Vitro Evaluation of a Retrievable Low-Profile Nitinol Vena Cava Filter", Journal of Vascular and Interventional Radiology, Apr. 2003, 14:469-474.

Bucker, A. et al., "Real-Time MR Guidance For Inferior Vena Cava Filter Placement in an Animal Model", Journal of Vascular and Interventional Radiology, Jun. 2001, 12:753-756.

Burbridge, B. E. et al., "Incorporation of The Gunther Temporary Inferior Vena Cava Filter Into The Caval Wall", Journal of Vascular and Interventional Radiology, Mar.-Apr. 1996, 7:289-290.

Cahn, M. D. et al., "Long Term Follow-up of Greenfield Inferior Vena Cava Filter Placement in Children", Journal of Vascular Surgery, Nov. 2001, 34:820-825.

Cain Jr., J.E. et al., "The Morbidity of Heparin Therapy After Development of Pulmonary Embolus in Patients Undergoing Thoracolumbar or Lumbar Spinal Fusion", Spine, vol. 20, No. 14, 1995, pp. 1600-1603.

Campbell, J. J. et al., "Aortic Pseudoaneurysm From Aortic Penetration With a Bird's Nest Vena Cava Filter", Journal of Vascular Surgery. Sep. 2003, 38:596-599.

Carabasi III, R. A. et al., "Complications Encountered With The Use of The Greenfield Filter", The American Journal of Surgery, Aug. 1987, Vo. 154, pp. 163-168.

Carlin, A. M. et al., "Prophylactic and Therapeutic Inferior Vena Cava Filters to Prevent Pulmonary Emboli in Trauma Patients", Archives of Surgery, May 2002, vol. 137, p. 521.

Chaturvedi, R. R. et al., "Intraoperative Apical Ventricular Septal Defect Closure Using a Modified Rashkind Double Umbrella", Heart, Oct. 1996, vol. 76, No. 4, pp. 367-369.

Cherian, J. et al., "Recurrent Pulmonary Embolism Despite Inferior Vena Cava Filter Placement in Patients With the Antiphospholipid Syndrome", Journal of Clinical Rheumatology, Feb. 2005, vol. 11, No. 1, pp. 56-58.

Cho, K. J. et al., "Evaluation of a New Percutaneous Stainless Steel Greenfield Filter", Journal of Vascular and Interventional Radiology, Mar.-Apr. 1997, 8:181-187.

Conners III, M. S et al., "Duplex Scan-Directed Placement of Inferior Vena Cava Filters: A Five-year Institutional Experience", Journal of Vascular Surgery, Feb. 2002, vol. 35, No. 2, pp. 286-291.

Couch, G. G. et al., "An In Vitro Comparison of The Hemodynamics of Two Inferior Vena Cava Filters", Journal of Vascular Surgery, Mar. 2000, 31:539-549.

Couch, G. G. et al., "In Vitro Assessment of The Hemodynamic Effects of a Partial Occlusion in a Vena Cava Filter", Journal of Vascular Surgery, Apr. 1997, vol. 25, No. 4, pp. 663-672.

Crochet, D. et al., "Evaluation of The LGM Vena-Tech Infrarenal Vena Cava Filter in an Ovine Venous Thromboembolism Model", Journal of Vascular Interventional Radiology, Jun. 2001, 12:739-745.

Crochet, D. P. et al., "Long-Term Follow-Up of Vena Tech-LGM Filter: Predictors and Frequency of Caval Occlusion", Journal of Vascular Interventional Radiology, Feb. 1999, 10:137-142.

Crochet, D. P. et al., "Vena Tech-LGM Filter: Long-Term Results of a Prospective Study", Radiology, 1993, 188:857-860.

Cvoro,V. et al., "Inferior Vena Caval Filters or Anticoagulation For Patients With Haemorrhagic Stroke Complicated By Venouse Thromboembolism?", Age and Ageing, Mar. 2002, vol. 32, No. 2, Research Library, pp. 85-86.

Danetz, J. S. et al., "Selective Venography Versus Nonselective Venography Before Vena Cava Filter Placement: Evidence For More, Not Less", Journal of Vascular Surgery, Nov. 2003, Vo. 38, No. 5, pp. 928-934.

Dick, A. et al., "Declotting of Embolized Temporary Vena Cava Filter By Ultrasound And The Angiojet: Comparative Experimental In Vitro Studies", Investigative Radiology, Feb. 1998, vol. 33(2), pp. 91-97.

Gabelmann, A. et al., "Percutaneous Retrieval of Lost of Misplaced Intravascular Objects", American Journal of Radiology, Jun. 2001, 176:1509-1513.

Gelbfish, G. A. et al., "Intracardiac and Intrapulmonary Greenfield Filters: A Long-Term Follow-Up", Journal of Vascular Surgery, Nov. 1991, Vo. 14, No. 5, pp. 614-617.

Girard, T. D. et al., "Prophylactic Vena Cava Filters For Trauma Patients: A Systematic Review of The Literature", Thrombosis Research, 2003, 112:261-267.

Greenfield, L. J. et al., "Experimental Embolic Capture By Asymmetric Greenfield Filters", Journal of Vascular Surgery, Sep. 1992, vol. 16, No. 3, pp. 436-444.

Kronemyer, B., Temporary Filter Traps Pulmonary Emboly, Orthopedics Today, p. 34.

Kuszyk, B. et al., "Subcutaneously Tethered Temporary Filter: Pathologic Effects in Swine", Journal of Vascular and Interventional Radiology, Nov.-Dec. 1995, Vo. 6, No. 6, pp. 895-902.

Mobin-Uddin, K. et al., "Evolution of a New Device For the Prevention of Pulmonary Embolism", The American Journal of Surgery, Oct. 1994, vol. 168, pp. 330-334.

Patterson, R. B. et al., "Case Reports: Repositioning of Partially Dislodged Greenfield Filters From the Right Atrium by Use of a Tip Deflection Wire", Journal of Vascular Surgery, Jul. 1990, vol. 12, No. 1, pp. 70-72.

Rogers, F. B. et al., "Immediate Pulmonary Embolism After Trauma: Case Report", Journal of Trauma: Injury, Infection, and Critical Care, vol. 48, No. 1, pp. 146-148.

Salamipour, H. et al., "Percutaneous Transfemoral Retrieval of a Partially Deployed Simon-Nitinol Filter Misplaced Into the Ascending Lumbar Vein", Journal of Vascular and Interventional Radiology, 1996, 7:917-919.

Savin, M. A. et al., "Greenfield Filter Fixation in Large Vena Cavae", Journal of Vascular and Interventional Radiology, 1998,9:75-80.

Schanzer, H. et al., "Guidewire Entrapment During Deployment of the Over-the-Guidewire Stainless Steel Greenfield Filter: A Device Design-Related Complication", Journal of Vascular Surgery, 2000, 31:607-610.

Sharafuddin, M. J. et al., "Endovascular Management of Venous Thrombotic and Occlusive Diseases of the Lower Extremities", Journal of Vascular and Interventional Radiology, Apr. 2003, 14:405-423.

Shellock, F. G. et al., "MR Procedures: Biologic Effects, Safety, and Patient Care", Radiology, 2004, 232:635-652.

"Staff Development Special, Get the Edge on Deep Vein Thrombosis", Nursing Management, Jan. 2004, pp. 21-29.

Taheri, S. A. et al., "Case Report: A Complication of The Greenfield Filter: Fracture And Distal Migration of Two Struts-A Case Report", Journal of Vascular Surgery, Jul. 1992, vol. 16, No. 1, pp. 96-99.

Tardy, B. et al, "Older People Included in a Venous Thrombo-Embolism Clinical Trial: A Patients' Viewpoint", Age and Ageing, 2003, 32:149-153.

Teitelbaum, G. P. et al., Low-Artifact Intravascular Devices: MR Imaging Evaluation, Radiology, Sep. 1988, 168:713-719.

Trerotola, S. O. et al., "Mechanical Thrombolysis of Venous Thrombosis in an Animal Model With Use of Temporary Caval Filtration", Journal of Vascular and Interventional Radiology, Sep. 2001, 12:1075-1085.

Uflacker, R., "Interventional Therapy For Pulmonary Embolism", Journal of Vascular Interventional Radiology, Feb. 2001, 12:147-164.

Weeks, S. M. et al., "Primary Gianturco Stent Placement for Inferior Vena Cava Abnormalities Following Liver Transplantation", Journal of Vascular and Interventional Radiology, Feb. 2000, 11:177-187.

AbuRahma, A.F. et al., "Endovascular Caval Interruption in Pregnant Patients With Deep Vein Thrombosis of the Lower Extremity", Journal of Vascular Surgery, 2001, 33:375-378.

Allen, T.L. et al., "Retrievable Vena Cava Filters in Trauma Patients For High-Risk Prophylaxis and Prevention of Pulmonary Embolism", The American Journal of Surgery, 2005, 189:656-661.

Arcasoy, S.M. et al., "Thrombolytic Therapy of Pulmonary Embolism", Chest, 1999, 115:1695-1707.

Arnold, D.M. et al., "Missed Opportunities For Prevention of Venous Thromboembolism", Chest, 2001, 120:1964-1971.

Brasel, K.J. et al., "Cost-Effective Prevention of Pulmonary Embolus in High-Risk Trauma Patients", The Journal of Trauma: Injury, Infection, and Critical Care, Mar. 1997, vol. 42, No. 3, pp. 456-462.

Buerger, P.M. et al., "Risk of Pulmonary Emboli in Patients With Pelvic Fractures", The American Surgeon, Aug. 1993, vol. 59, pp. 505-508.

Darcy, M.D. et al., "Short-Term Prophylaxis of Pulmonary Embolism by Using a Retrievable Vena Cava Filter", American Journal of Roentgenology, 1986, 147:836-838.

David, W. et al., "Pulmonary Embolus After Vena Cava Filter Placement", The American Surgeon, Apr. 1999, vol. 65, pp. 341-346.

Ferraro, F. et al., "Thromboembolism in Pregnancy: A New Temporary Caval Filter", Miverva Anestesiologica, 2001, vol. 67, No. 5, pp. 381-385.

Georgopoulos, S.E. et al., "Paradoxical Embolism", Journal of Cardiovascular Surgery, 2001, 42:675-677.

Goldhaber, S.Z. et al., "Acute Pulmonary Embolism: Part II Risk Stratification, Treatment, and Prevention", Circulation, 2003, 108:2834-2838.

Goldhaber, S.Z., "A Free-Floating Approach to Filters", Archives of Internal Medicine, Feb. 10, 1997, vol. 157, No. 3, pp. 264-265.

Goldhaber, S.Z., "Venous Thromboembolism in the Intensive Care Unit: The Last Frontier For Pro . . . ", Chest, Jan. 1998, 113(1):5-7.

Goldman, H.B. et al., "Ureteral Injury Secondary to an Inferior Vena Caval Filter", The Journal of Urology, Nov. 1996, vol. 156, No. 5, p. 1763.

Golueke, P.J. et al., "Interruption of the Vena Cava by Means of the Greenfield Filter: Expanding the Indications", Surgery, Jan. 1988, vol. 103, No. 1, pp. 111-117.

Gonze, M.D. et al., "Orally Administered Heparin for Preventing Deep Venous Thrombosis", American Journal of Surgery, Aug. 1998, vol. 176, pp. 176-178.

Goodman, L.R. et al., "Subsequent Pulmonary Embolism: Risk After a Negative Helical CT Pulmonary Angiogram-Prospective Comparison With Scintigraphy", Radiology, 2000, 215:535-542.

Gottlieb, R.H., "Randomized Prospective Study Comparing Routine Versus Selective Use of Sonography of the Complete Calf in Patients With Suspected Deep Venous Thrombosis", American Journal of Roentgenology, Jan. 2003, 180:241-245.

Grandes, O.H. et al., "Deep Venous Thrombosis in the Pediatric Trauma Population: An Unusual Event: Report of Three Cases", The American Surgeon, Mar. 2000, vol. 66, pp. 273-276.

Grassi, C.L. et al., "Quality Improvement Guidelines for Percutaneous Permanent Inferior Vena Cava Filter Placement for the Prevention of Pulmonary Embolism", Journal of Vascular and Interventional Radiology, Sep. 2003, 14:S271-S275.

Grassi, C.L. et al., "Vena Caval Occlusion After Simon Nitinol Filter Placement: Identification With MR Imaging In Patients With Malignancy", Journal of Vascular and Interventional Radiology, 1992, 3(3):535-539.

Greene, F.L. et al., Letters to the Editor, The Journal of Trauma: Injury, Infection, and Critical Care, May 2005, vol. 5 8, No. 5, pp. 1091-1092.

Greenfield, L.J. et al., "Free-Floating Thrombus and Pulmonary Embolism/Reply", Archives of Internal Medicine, Dec. 8-22, 1997, pp. 2661-2662.

Greenfield, L.J. et al., "Limb Asymmetry in Titanium Greenfield Filters: Clinically Significant?", Journal of Vascular Surgery, 1997, 26:770-775.

Greenfield, L.J. et al., "Prophylactic Vena Caval Filters in Trauma: The Rest of the Story", Journal of Vascular Surgery, 2000, 32:490-497.

Greenfield, L.J. et al., "Recommended Reporting Standards for Vena Caval Filter Placement and Patient Follow-Up", Journal of Vascular and Interventional Radiology, 1999,10:1013-1019.

Greenfield, L.J. et al., "Results of a Multicenter Study of The Modified Hood-Titanium Greenfield Filter", Journal of Vascular Surgery, 1991, 14:253-257.

Greenfield, L.J. et al., "The Percutaneous Greenfield Filter: Outcomes and Practice Patterns", Journal of Vascular Surgery, 2000, 32:888-893.

Greenfield, L.J. et al., "Twenty-Year Clinical Experience With the Greenfield Filter", Cardiovascular Surgery, Apr. 1995, vol. 3, No. 2, pp. 199-205.

Greenfield, L.J., "Cost vs Value in Vena Caval Filters", Chest, Jul. 1998, vol. 114, No. 1, pp. 9-10.

Greenfield, L.J., "Current Indications For and Results of Greenfield Filter Placement", Journal Vascular Surgery, May 1984, vol. 1, No. 3, pp. 502-504.

Greenfield, L.J., "Does Cervical Spinal Cord Injury Induce Higher Incidence of Complications After Prophylactic Greenfield Filter Usage?", Journal of Vascular and Interventional Radiology, Jul.-Aug. 1997, pp. 719-720.

Greenfield, L.J., "Recurrent Thromboembolism in Patients With Vena Cava Filters", Journal of Vascular Surgery, 2001, 33:510-514.

Greenfield, L.J., "Results of a Multi-Center Study of the Modified Hook-Titanium Greenfield Filter", Journal of Vascular Surgery, Sep. 1991.

Greenfield, L.J., "Staging of Fixation and Retrievability of Greenfield Filters", Journal of Vascular Surgery, Nov. 1994, vol. 20, No. 5, pp. 744-750.

Hagspiel, K.D. et al., "Inferior Vena Cava Filters: An Update", Applied Radiology, Nov. 1998, pp. 20-34.

Hagspiel, K.L. et al., "Difficult Retrieval of a Recovery IVC Filter", Journal of Vascular and Interventional Radiology (Letters to the Editor), Jun. 2004, vol. 15, No. 6, pp. 645-650.

Hainaux, B. et al., "Intragastric Band Erosion After Laparoscopic Adjustable Gastric Banding for Morbid Obesity: Imaging Characteristics of an Underreported Complication", American Journal of Roentgenology, Jan. 2005, 184:109-112.

Harold, K.L. et al., "Laparoscopic Approach to Open Gastric Bypass", The American Journal of Surgery, 2002, 184:61-62.

Harries, S.R., "Long-Term Follow-Up of the Antheor Inferior Vena Cava Filter", Clinical Radiology, 1998, 53:350-352.

Hastings, G.S. et al., "Repositioning the 12-F Over-the-Wire Greenfield Filter", Journal of Vascular and Interventional Radiology, 2000, 11:1207-1210.

Hill, S.L. et al., "Deep Venous Thrombosis in the Trauma Patient", The American Surgeon, Jun. 1994, vol. 60, pp. 405-408.

Hingorani, A. et al., "Upper Extremity Deep Venous Thrombosis and Its Impact on Morbidity and Mortality Rates in a Hospital-Based Population", Journal of Vascular Surgery, Nov. 1997, 26:853-860.

Holtzman, R.B. et al., "Comparison of Carbon Dioxide and Iodinated Contrast for Cavography Prior to Inferior Vena Cava Filter Placement", The American Journal of Surgery, 2003, 185:364-368.

Hosaka, J. et al., "Placement of a Spring Filter During Interventional Treatment of Deep Venous Thrombosis to Reduce the Risk of Pulmonary Embolism", ACTA Radiologica, 1999, 40:545-551.

Hughes, G.C. et al., "The Use of a Temporary Vena Caval Interruption Device in High-Risk Trauma Patients Unable to Receive Standard Venous Thromboembolism Prophylaxis", Investigative Radiology, Feb. 1999, vol. 46, No. 2, pp. 246-249.

Hunter, D.W. et al., "Retrieving the Amplatz Retrievable Vena Cava Filter", Cardiovascular and Interventional Radiology, 1987, 10:32-36.

Jackson Slappy, A.L. et al., "Delayed Transcaval Renal Penetration of a Greenfield Filter Presenting as Symptomatic Hydronephrosis", The Journal of Urology, Apr. 2002, vol. 167, pp. 1778-1779.

Jaeger, H.J. et al., "A Physiologic In Vitro Model of the Inferior Vena Cava With a Computer-Controlled Flow System for Testing of Inferior Vena Cava Filters", Investigative Radiology, Sep. 1997, vol. 32, No. 9, pp. 511-522.

Johnson, S.P. et al., "Single Institution Prospective Evaluation of the Over-The-Wire Greenfield Vena Caval Filter", Journal of Vascular and Interventional Radiology, 1998, 9:766-773.

Jones, A.L. et al., "Case Report: Use of an IVC Filter in The Management of IVC Thrombosis Occurring as a Complication of Acute Pancreatitis", Clinical Radiology, 1998, 53:462-464.

Joshi, A. et al., "Filter-Related, Thrombotic Occlusion of The Inferior Vena Cava Treated With a Gianturco Stent", Journal of Vascular and Interventional Radiology, 2003, 14:381-385.

Kasirajan, K. et al., "Percutaneous AngioJet Thrombectomy in the Management of Extensive Deep Venous Thrombosis", Journal of Vascular and Interventional Radiology, 2001, 12:179-185.

Katsamouris, A.A. et al., "Inferior Vena Cava Filters: In Vitro Comparison of Clot Trapping And Flow Dynamics", Radiology, 1988, 166:361-366.

Kaufman, J.A. et al., "Guide-Wire Entrapment by Inferior Vena Caval Filters: In Vitro Evaluation", Radiology, 1996, 198:71-76.

Kaufman, J.A. et al., "Operator Errors During Percutaneous Placement of Vena Cava Filters", American Journal of Roentgenology, Nov. 1995, 165:1281-1287.

Kaw, L.L., Jr. et al., "Use of Vena Cava Filters", Techniques in Orthopaedics, 2004, 19(4):327-336.

Kercher, K. et al., "Overview of Current Inferior Vena Cava Filters", The American Surgeon, Aug. 2003, vol. 69, pp. 643-648.

Kerlan, R.K., Jr. et al., "Residual Thrombus Within a Retrievable IVC Filter", Journal of Vascular and Interventional Radiology, 16:555-557.

King, J.N. et al., "Vena Cava Filters", The Western Journal of Medicine, Mar. 1992, vol. 156, No. 3, pp. 295-296.

Kinney, T.B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.

Kinney, T.B. et al., "Fatal Paradoxic Embolism Occurring During IVC Filter Insertion in a Patient With Chronic Pulmonary Thromboembolic Disease", Journal of Vascular and Interventional Radiology, 2001, 12:770-772.

Kinney, T.B., "Translumbar High Inferior Vena Cava Access Placement in Patients With Thrombosed Inferior Vena Cava Filters", Journal of Vascular and Interventional Radiology, 2003, 14:1563-1567.

Kinney, T.B., "Update on Inferior Vena Cava Filters", Journal of Vascular and Interventional Radiology, 2003, 14:425-440.

Kozak, T.K.W. et al., "Massive Pulmonary Thromboembolism After Manipulation of an Unstable Pelvic Fracture: A Case Report And Review of the Literature", The Journal of Trauma: Injury, Infection, And Critical Care, 1995, vol. 38, pp. 366-367.

Kraimps, J. et al., "Optical Central Trapping (OPCETRA) Vena Caval Filter: Results of Experimental Studies", Journal of Vascular and Interventional Radiolory, 1992, 3:697-701.

Kupferschmid, J.P. et al., "Case Report: Small-Bowel Obstruction From an Extruded Greenfield Filter Strut: An Unusual Late Complication", Journal of Vascular Surgery, Jul. 1992, vol. 16, No. 1, pp. 113-115.

Kurgan, A. et al., "Case Reports: Penetration of The Wall of an Abdominal Aortic Aneurysm By a Greenfield Filter Prong: A Late Complication", Journal of Vascular Surgery, Aug. 1993, vol. 18, No. 2, pp. 303-306.

Kuszysk, B. et al., "Subcutaneously Tethered Temporary Filter: Pathologic Effects in Swine", Journal of Vascular and Interventional Radiology, Nov.-Dec. 1995, vol. 6, No. 6, pp. 895-902.

Leask, R.L. et al., "Hemodynamic Effects of Clot Entrapment in the TrapEase Inferior Vena Cava Filter", Journal of Vascular and Interventional Radiology, 2004, 15:485-490.

Leask, R.L. et al., "In Vitro Hemodynamic Evaluation of a Simon Nitinol Vena Cava Filter: Possible Explanation of IVC Occlusion", Journal of Vascular and Interventional Radiology, 2001, 12:613-618.

Lemmon, G.W. et al., "Incomplete Caval Protection Following Suprarenal Caval Filter Placement", Angiology the Journal of Vascular Diseases, Feb. 2000, vol. 51, No. 2, pp. 155-159.

Lin, M. et al., "Successful Retrieval of Infected Gunther Tulip IVC Filter", Journal of Vascular and Interventional Radiology, 2000, 11:1341-1343.

Lipman, J.C., "Removal of Vena Caval Filter at 224 Days", Southern Medical Journal, May 2005, vol. 98, No. 5, pp. 556-558.

Loehr, S.P. et al., "Retrieval of Entrapped Guide Wire in an IVC Filter Facilitated With Use of a Myocardial Biopsy Forceps and Snare Device", Journal of Vascular and Interventional Radiology (Letter to Editor), Sep. 2001, vol. 12, No. 9, pp. 1116-1118.

Lorch, H. et al., "Current Practice of Temporary Vena Cava Filter Insertion: A Multicenter Registry", Journal of Vascular and Interventional Radiology, 2001, 11:83-88.

Lorch, H. et al., "Temporary Vena Cava Filters and Ultrahigh Streptokinase Thrombolysis Therapy: A Clinical Study", Cardiovascular Interventional Radiology, 2000, 23:273-278.

Lund, G. et al., "A New Vena Caval Filter for Percutaneous Placement and Retrieval Experiemental Study", Radiology, 1984, 152:369-372.

Lund, G. et al., "Retrievable Vena Caval Filter Percutaneously Introduced", Radiology, 1985, vol. 155, p. 831.

Machado, L.G. et al., "Medical Applications of Shape Memory Alloys", Brazilian Journal of Medical and Biological Research, 2003, 36:683-691.

Magnant, J.G. et al., "Current Use of Inferior Vena Cava Filters", Journal of Vascular Surgery, Nov. 1992, vol. 16, No. 5, pp. 701-706.

Marston, W.A. et al., "Re: Comparison of the AngioJet Rheolytic Catheter to Surgical Thrombectomy for the Treatment of Thrombosed Hemodialysis Grafts", Journal of Vascular and Interventional Radiology (Letters to the Editor), Sep. 2000, vol. 11, No. 8, pp. 1095-1099.

McCowan, T.C. et al., "Complications of the Nitinol Vena Caval Filter", Journal of Vascular and Interventional Radiology, 1992, 3:401-408.

Melinek, J. et al., "Autopsy Findings Following Gastric Bypass Surgery For Morbid Obesity", Arch Path Lab Med, 2002 126:1091-1095.

Mihara, H. et al., "Use of Temporary Vena Cava Filters After Catheter-Directed Fragmentation and Thrombolysis in Patients With Acute Pulmonary Thromboembolism", Japanese Circulation Journal, Jun. 1998, vol. 62, pp. 462-464.

Millward, S.F. et al., "Preliminary Clinical Experience with the Gunther Temporary Inferior Vena Cava Filter", Journal of Vascular and Interventional Radiology, 1994, 5:863-868.

Millward, S.F. et al., "Gunther Tulip Filter" Preliminary Clinical Experience With Retrieval, Journal of Vascular and Interventional Radiology, 2000, 11:75-82.

Millward, S.F. et al., "Gunther Tulip Retrievable Vena Cava Filter: Results From the Registry of the Canadian Interventional Radiology Association", Journal of Vascular and Interventional Radiology, 2001, 12:1053-1058.

Millward, S.F. et al., "LGM (Vena Tech), Vena Caval Filter: Clinical Experience in 64 Patients", Journal of Vascular and Interventional Radiology, Nov. 1991, 2:429-433.

Millward, S.F. et al., "LGM (Vena Tech), Vena Caval Filter: Experience at a Single Institution", Journal of Vascular and Interventional Radiology, Mar.-Apr. 1994, 5:351-356.

Millward, S.F. et al., "Reporting Standards For Inferior Venal Caval Filter Placement and Patient Follow-Up: Supplement for Temporary and Retrievable/Optional Filters", Journal of Vascular and Interventional Radiology, Apr. 2005, 16:441-443.

Millward, S.F., "Gunther Tulip Retrievable Filter" Why, When and How?, JACR, Jun. 2001, vol. 52, No. 3, pp. 188-192.

Millward, S.F., "Temporary and Retrievable Inferior Vena Cava Filters" Current Status, Journal of Vascular and Interventional Radiology, May-Jun. 1998, vol. 9, No. 3, pp. 381-387.

Mobin-Uddin, K. et al., "Evolution of a New Device For the Prevention of Pulmonary Embolism", The American Journal of Surgery, vol. 168, Oct. 1994, pp. 330-334.

Mohan, C.R. et al., "Comparative Efficacy And Complications of Vena Caval Filters", Journal of Vascular Surgery, 1995, 21:235-236.

Montessuit, M. et al., "Screening For Patent Foramen Ovale and Prevention of Paradoxical Embolus", Ann Fasc Surg, 1997, 11:168-172.

Montgomery, K.D. et al., The Detection and Management of Proximal Deep Venous Thrombosis in Patients With Acute Acetabular Fractures: A Follow-up Report:, Journal of Orthopedic Trauma, Jul. 1997, 1(5):330-336.

Munir, M.A. et al., "An In Situ Technique to Retrieve an Entrapped J-Tip Guidewire From an Inferior Vena Cava Filter", Anesth Analo, 2002, 95:308-309.

Stosslein, F. et al., "A Rare Complication With an Antheor Vena Cava Filter", Cardiovascular and Interventional Radiology, 1998, 21:165-167.

Wholey, M. et al., "Technique or Retrieval of a Guidewire Lodged in a Vena Cava Filter", Vascular and Endovascular Surgery, 2002, vol. 36, No. 5, pp. 385-387.

AbuRahma, A.F. et al., "Management of Deep Vein Thrombosis of the Lower Extremity in Pregnancy: A Challenging Dilemma", The American Surgeon, Feb. 1999, vol. 65, No. 2, pp. 164-167A.

AbuRahma, F. et al., "Etiology of Peripheral Arterial Thromboembolism in Young Patients", The American Journal of Surgery, vol. 176, Aug. 1998, pp. 158-161.

Adams, E. et al., "Retrievable Inferior Vena Cava Filter For Thrombolic Disease in Pregnancy", British Journal of Obstetrics and Gynaecology, Sep. 1998, vol. 105, pp. 1039-1042.

Ahearn, G.S. et al., "Massive Pulmonary Embolism During Pregnancy Successfully Treated With Recombinant Tissue Plasminogen Activator", Archives of Interal Medicine, Jun. 10, 2002, 162(11):1221-1227.

American Gastroenterological Association Clinical Practice Committee, Americal Gastroenterological Associattion, Sep. 2002 123:883-932.

Anderson, J.T. et al., "Bedside Noninvasive Detection of Acute Pulmonary Embolism in Critically III Surgical Patients", Archives of Surgery, Aug. 1999, 134(8):869-875.

Anthone, G.J. et al., The Duodenal Switch Operation For the Treatment of Morbid Obesity, Annals of Surgery, Oct. 2003, 238(4):618-628.

Arcelus, J.I. et al, "The Management And Outcome of Acute Venous Thromboembolism: A Prospective Registry Including 4011 Patients", Journal of Vascular Surgery, 2003, 38:916-922.

Authors' Abstract, "Abstracts of Current Literature", Journal of Vascular and Interventional Radiology, Oct. 2003, vol. 14, No. 10, pp. 1351-1357.

Authors' Abstracts, "Abstract of Current Literature", Journal of Vascular and Interventional Radiology, Apr. 2004, pp. 408-415.

Bass, B.L., "What's New in General Surgery: Gastrointestinal Conditions", The Journal of American College Surgeons, Dec. 2002, vol. 195, No. 6, pp. 835-854.

Bendick, P.J. et al., Serial Duplex Ultrasound Examination For Deep Vein Thrombosis in Patients With Suspected Pulmonary Embolism, Journal of Fascular Surgery, Nov. 1996, vol. 24, No. 5, pp. 732-737.

Bessoud, B. et al., Experience at a Single Institution With Endovascular Treatment of Mechanical Complications Caused by Implanted Central Venous Access Devices in Pediatric and Adult Patients, American Journal of Roentgenology, Feb. 2003, 180:527-532.

Bevoni, L., "Management of Adult Obesity", Clinician Reviews, May 2003, 13(5):56-62.

Biertho, L. et al., "Laparoscopic Gastric Bypass Versus Laparoscopic Adjustable Gastric Banding: A Comparative Study of 1,200 Cases", Journal of the American Colloge of Surgeons, Oct. 2003, vol. 197, No. 4, pp. 536-545.

Blachar A. et al., "Gastrointestinal Complications of Laparoscopic Roux-en-Y Gastric Bypass Surgery in Patients Who Are Morbidly Obese: Findings on Radiography and CT", American Journal of Roentgenology, Dec. 2002, 179:1437-1442.

Blachar, A. et al., "Gastrointestinal Complications of Laparoscopic Roux-en-Y Gastric Bypass Surgery: Clinical and Imaging Findings", Radiology, 2002, 223:625-632.

Blaszyk, H. et al., "Factor V Leiden and Morbid Obesity in Fatal Postoperative Pulmonary Embolism", Archives of Surgery, Dec. 2000, 135(12):1410-1413.

Bovyn, G. et al., "The Tempofilter®: A Multicenter Study of a New Temporary Caval Filter Implantable For up to Six Weeks", Annals of Vascular Surgery, 1997, 11:520-528.

Bridges, G.G. et al., "Expedited Discharge in Trauma Patients Requiring Anticoagulation for Deep Venous Thrombosis Prophylaxis: The LEAP Program", The Journal of Trauma: Injury, Infection and Critical Care, Feb. 2003, vol. 54, No. 2, pp. 232-235.

Brolin, R.E., "Laparoscopic Verses Open Gastric Bypass to Treat Morbid Obesity", Annals of Surgery, Apr. 2004, vol. 239, No. 4, pp. 438-440.

Capella, J.F. et al., An Assessment of Vertical Banded Gastroplasty-Roux-en-Y Gastric Bypass For The Treatment of Morbid Obesity.

Carter, Y. et al., "Deep Venous Thrombosis and ABO Blood Group Are Unrelated in Trauma Patients", The Journal of Trauma: Injury, Infection, and Critical Care, 2002, 52:112-116.

Castaneda, F. et al., "Catheter-Directed Thrombolysis in Deep Venous Thrombosis With Use of Reteplase: Immediate Results And Complications From a Pilot Study", Journal of Vascular and Interventional Radiology, 2002, 13:577-580.

Ceelen, W. et al., "Surgical Treatment of Severe Obesity With A Low-Pressure Adjustable Gastric Band, Experimental Data and Clinical Results in 625 Patients", Annals of Surgery, 2003, 237(1):10-16.

Chanduszko, A., "Determination of Nitinol Transition Temperatures Using a Dynamical Mechanical Analyzer", The International Conference on Shape Memory and Superelastic Technology, 2000 Conference Proceedings, 2001, pp. 375-381.

Chengelis, D.L. et al., "Progression of Superficial Venous Thrombosis to Deep Vein Thrombosis", Journal of Vascular Surgery, 1996, 24:745-749.

Choban, P.S. et al., "The Impact of Obesity on Surgical Outcomes: A Review, "Journal of the American College of Surgeons, Dec. 1997, vol. 185, pp. 593-603.

Chung, J.W. et al., "Acute Iliofemoral Deep Vein Thrombosis: Evaluation of Underlying Anatomic Abnormalities by Spiral CT Venography", Journal of Vascular and Interventional Radiology, 2004, 15:249-256.

Clarke, C.S. et al., "Puerperal Ovarian Vein Thrombosis With Extension Into The Inferior Vena Cava", The American Surgeon, Feb. 1999, vol. 65, No. 2, pp. 147-150.

Cooper, S.G. et al., "Distal Retraction and Inversion of the Simon Nitinol Filter During Surgical Venous Procedures: Report of Two Cases", Journal of Vascular and Interventional Radiology, 1997, 8:433-435.

Cottam, D.R. et al., "Laparoscopic Era of Operations For Morbid Obesity", Archives of Surgery, Apr. 2003, 138(4):367-375.

Cragg, A. et al., "A New Percutaneous Vena Cava Filter", American Journal of Roentgenology, Sep. 1983, 141:601-604.

Dabbagh, A. et al., "Late Complication of a Greenfield Filter Associating Caudal Migration And Perforation of The Abdominal Aorta by a Ruptured Strut", Journal of Vascular Surgery, Aug. 1995, vol. 22, No. 2, pp. 182-187.

Dake, M.D. et al., "Thrombolytic Therapy in Venous Occlusive Disease", Journal of Vascular and Interventional Radiology, 1995, 6:73S-77S.

Delman, R. et al., "Cerebrovascular Accident After Greenfield Filter Placement For Paradoxical Embolism", Journal of Vascular Surgery, Mar. 1989, vol. 9, No. 3, pp. 452-454.

Davidson, B.L., "DVT Treatment in 2000: State of the Art", Orthopedics, Jun. 2000, 23(6):pp. S651-s654.

De Gregorio, M.A. et al., "Animal Experience in The Gunther Tulip Retrievable Inferior Vena Cava Filter", Cardiovascular and Interventional Radiology, Nov. 2001, 24:413-417.

De Gregorio, M.A. et al., "Mechanical And Enzymatic Thrombolysis For Massive Pulmonary Embolism", Journal of Vascular and Interventional Radiology, 2002, 13:163-169.

Debing, E. et al., "Popliteal Venous Aneurysm With Pulmonary Embolism", Journal of Cardiovascular Surgery, Oct. 1998, vol. 39, No. 5, pp. 569-572.

Decousus, H. et al., "A Clinical Trial of Vena Caval Filters in The Prevention of Pulmonary Embolism in Patients With Proximal Deep-Vein Thrombosis", The New England Journal of Medicine, Feb. 12, 1998, vol. 338, No. 7, pp. 409-415.

DeMaria, E.J. et al., "Results of 281 Consecutive Total Laparoscopic Roux-en-Y Gastric Bypasses to Treat Morbid Obesity", Annals of Surgery, 2002, vol. 235, No. 5 pp. 640-647.

Dennis, J.W. et al., "Efficacy of Deep Venous Thrombosis Prophylaxis in Trauma Patients and Identification of High-Risk Groups", The Journal of Trauma, 1993, vol. 35, No. 1, pp. 132-137.

Denny, D.F. Jr., "Errant Percutaneous Greenfield Filter Placement Into The Retroperitoneum" Journal of Vascular Surgery Jun. 1991, vol. 13, No. 6.

Dewald, C.L. et al., Vena Cavography With $CO_2$ Versus With Iodinated Contrast Material For Inferior Vena Cava Filter Placement: A Prospective Evaluation, Radiology, 2000, 216:752-757.

Dibie, A. et al., "In Vivo Evaluation of a Retrievable Vena Cava Filter-The Dibie-Musset Filter: Experimental Results", Cardiovascular and Interventional Radiology, 1998, 21:151-157.

Duperier, T. et al., "Acute Complications Associated With Greenfield Filter Insertion i High-Risk Trauma Patients", The Journal of Trauma: Injury, Infection, and Critical Care, Mar. 2003, vol. 54, No. 3, pp. 545-549.

Edlow, J.A., "Emergency Department Management of Pulmonary Embolism", Emergency Medicine Clinics of North America, Nov. 2001, vol. 19, No. 4, pp. 995-1011.

Egermayer, P., "Follow-Up For Death or Recurrence Is Not a Reliable Way of Assessing the Accuracy of Diagnostic Tests For Thromboembolic Disease", Chest 1997, 111:1410-1413.

Ekim, N. et al., "Pulmonary Thromboembolism With Massive Vaginal Bleeding Due to Thrombolytic Therapy", Respirology, 2003, 8:246-248.

Engmann, E. et al., "Clinical Experience With The Antecubital Simon Nitinol IVC Filter", Journal of Vascular and Interventional Radiology, 1998, 9:774-778.

Fava, M. et al., "Massive Pulmonary Embolism: Percutaneous Mechanical Thrombectomy During Cardiopulmonary Resuscitation", Journal of Vascular and Intervention Radiology, 2005, 16:119-123.

Fava, M. et al., "Massive Pulmonary Embolism: Treatment With The Hydrolyser Thrombectomy Catheter", Journal of Vascular and Intervention Radiology, 2000, 11:1159-1164.

Feezor, R.J. et al., "Duodenal Perforation With an Inferior Vena Cava Filter: An Unusual Cause of Abdominal Pain", Journal of Vascular Surgery, 2002, pp. 1-3.

Fernandez, A.Z. Jr. et al., "Multivariate Analysis of Risk Factors For Death Following Gastric Bypass For Treatment of Morbid Obesity", Annals of Surgery, May 2004, vol. 239, No. 5, pp. 698-703.

Ferral, H., "Regarding "Lessons Learned From a 6-Year Clinical Experience With Superior Vena Cava Greenfield Filters"", Journal of Vascular Surgery, Apr. 2001, vol. 33, No. 4.

Ferris, E.J. et al., "Percutaneous Inferior Vena Caval Filters: Follow-Up of Seven Designs in 320 Patients", Radiology 1993, 188:851-856.

Fink, S. et al., "Pulmonary Embolism and Malpractice Claims", Southern Medical Journal, Dec. 1998, vol. 91, No. 12, pp. 1149-1152.

Foley, M. et al., "Pulmonary Embolism After Hip or Knee Replacement: Postoperative Changes on Pulmonary Scintigrams in Asymptomatic Patients", Radiology, 1989, 172:481-485.

Fraser, J.D. et al., "Deep Venous Thrombosis: Recent Advances and Optimal Investigation With US", Radiology, 1999, 211:9-24.

Frezza, E.E. et al., "Entrapment of a Swan Ganz Catheter in an IVC Filter Requiring Caval Exploration", Journal of Cardiovascular Surgery, 1999, 40:905-908.

Friedell, M.L. et al., "Case Report: Migration of a Greenfield Filter to the Pulmonary Artery: Case Report", Journal of Vascular Surgery, Jun. 1986, vol. 3, No. 6, pp. 929-931.

Friedland, M. et al., "Vena Cava Duplex Imaging Before Caval Interruption", Journal of Vascular Surgery, Oct. 1995, vol. 24, No. 4, pp. 608-613.

Gamblin, T.C. et al., "A Prospective Evaluation of a Bedside Technique For Placement of Inferior Vena Cava Filters: Accuracy and Limitations of Intravascular Ultrasound", The American Surgeon, May 2003, vol. 69, pp. 382-386.

Garcia, N.D., "Is Bilateral Ultrasound Scanning of the Legs Necessary For Patients With Unilateral Symptons of Deep Vein Thrombosis", Journal of Vascular Surgery, 2001, 34:792-797.

Gayer, G. et al., "Congenital Anomalies of The Inferior Vena Cava Revealed on CT in Patients With Deep Vein Thrombosis", American Journal of Roentgenology, Mar. 2003, vol. 180, pp. 729-732.

Geerts, W.H., "A Prospective Study of Venous Thromboembolism After Major Trauma", Dec. 15, 1994, vol. 331, No. 24, pp. 1601-1606.

Gelfand, E.V. et al., "Venous Thromboembolism Guidebook, Fourth Edition", Critical Pathways in Cardiology, Dec. 2003, vol. 2, No. 4, pp. 247-265.

Ginsberg, M.S. et al., "Clinical Usefulness of Imaging Performed After CT Angiography That Was Negative For Pulmonary Embolus in a High-Risk Oncologic Population", American Journal of Roentgenology, Nov. 2002, 179:1205-1208.

Girard, P. et al., Medical Literature and Vena Cava Filters*, Chest, 2002, 122:963-967.

Goldberg, M.E., "Entrapment of an Exchange Wire by an Inferior Vena Caval Filter: A Technique For Removal", Anesth Analg., Apr. 2003, 96:4, 1235-1236.

Greenfield, L.J. et al., "Filter Complications and Their Management", Seminars in Vascular Surgery, vol. 13, No. 3, Sep. 2000, pp. 213-216.

Hak, D.J., "Prevention of Venous Thromboembolism in Trauma and Long Bone Fractures", Current Opinion in Pulmonary Medicine, 2001, 7:338-343.

Hammond, F.M. et al., "Venous Thromboembolism in The Patient With Acute Traumatic Brain Injury: Screening, Diagnosis, Prophylaxis, and Treatment Issues", Journal of Head Trauma Rehabilitation, Feb. 1998, vol. 13, No. 1, pp. 36-48.

Hardhammar, P.A. et al., "Reduction in Thrombotic Events With Heparin-Coated Palmaz-Schatz Stents in Normal Porcine Coronary Arteries", Circulation, Feb. 1, 1996, vol. 93, No. 3, pp. 423-430.

Harris, E.J. Jr. et al., "Phlegmasia Complicating Prophylactic Percutaneous Inferior Vena Caval Interruption: A Word of Caution", Journal of Vascular Surgery, 1995, vol. 22, No. 5, pp. 606-611.

Hawkins, S.P. et al., "The Simon Nitinol Inferior Vena Cava Filter: Preliminary Experience in the UK", Clinical Radiology, 1992, 46:378-380.

Headrick, J.R. et al., "The Role of Ultrasonography and Inferior Vena Cava Filter Placement in High-Risk Trauma Patients", American Surgeon, Jan. 1997, vol. 63, Issue 1.

Helfet, D., Magnetic Resonance Venography to Evaluate Deep Venous Thrombosis in Patients With Pelvic and Acetabular Trauma, The Journal of Trauma: Injury, Infection, and Critical Care, Jul. 2001, p. 178.

Heng, J.T. et al., "Occlusion of Persistent Left Superior Vena Cava to Unroofed Coronary Sinus Using Vena Cava Filter and Coils", Hears, Jun. 1997, vol. 77, No. 6, pp. 579-580.

Henkle, G. et al., "Patterns of Referral For Inferior Vena Caval Filtration: Delays And Their Impact", American Journal of Roentgenology, Oct. 2004, 183:1021-1024.

Hicks, M.E. et al., "Prospective Anatomic Study of the Inferior Vena Cava and Renal Veins: Comparison of Selective Renal Venography With Cavography and Relevance in Filter Placement", Journal of Vascular and Interventional Radiology, 1995, 6:721-729.

Higa, K.D. et al., "Laparoscopic Roux-en-Y Gastric Bypass For Morbid Obesity", Archives of Surgery, Sep. 2000, vol. 135, No. 9, pp. 1029-1034.

Johnson, M.S., "Current Strategies For the Diagnosis of Pulmonary Embolus", Journal of Vascular and Interventional Radiology, 2002, 13:13-23.

Kaplan, S. et al., "Surgical Management of Renal Cell Carcinoma With Inferior Vena Cava Tumor Thrombus", The American Journal of Surgery, 2002, 183:292-299.

Karmy-Jones, R. et al., "Surgical Management of Cardiac Arrest Caused by Massive Pulmonary Embolism in Trauma Patients", The Journal of Trauma: Injury, Infection, and Critical Care, 2000, vol. 48, No. 3, pp. 519-520.

Kazmers, A. et al., "Duplex Examination of the Inferior Vena Cava", The American Surgeon, Oct. 2000, vol. 66, pp. 986-989.

Kazmers, A. et al., "Intraoperative Insertion of Greenfield Filters: Lessons Learned in a Personal Series of 152 Cases", The American Surgeon, Oct. 2002, vol. 68, pp. 877-882.

Kazmers, A. et al., "Pulmonary Embolism in Veterans Affairs Medical Centers: Is Vena Cava Interruption Underutilized?", The American Surgeon, Dec. 1999, vol. 65, No. 12, pp. 1171-1175.

Kearon, C. et al., "Management of Anticoagulation Before and After Elective Surgery", The New England Journal of Medicine, May 22, 1997, vol. 336, No. 21, pp. 1506-1511.

Kelly, J. et al., "Anticoagulation or Inferior Vena Cava Filter Placemente For Patients With Primary Intracerebral Hemorrhage Developing Venous Thromboembolism?" Stroke, 2003, 34:2999-3005.

Marret, H. et al., "Re: Metastatic Involvement of a Retrieved Inferior Vena Cava Filter", Journal of Vascular and Interventional Radiology, Jul. 2004, vol. 15, No. 7, pp. 775-776.

Matteson, B. et al., "Role of Venous Duplex Scanning in Patients With Suspected Pulmonary Embolism", The Journal of Vascular Surgery, 1996, 24:768-773.

Mattos, M.A. et al., "Prevalence and Distribution of Calf Vein Thrombosis in Patients With Symptomatic Deep Venous Thrombosis: A Color-Flow Duplex Study", Journal of Vascular Surgery, 1996, 24:738-744.

Maxwell, R.A. et al., "Routine Prophylactic Vena Cava Filtration is Not Indicated After Acute Spinal Cord Injury", The Journal of Trauma: Injury, Infection, and Critical Care, 2002, 52:902-906.

McMurtry, A.L. et al., "Increased Use of Prophylactic Vena Cava Filters in Trauma Patients Failed to Decrease Overall Incidence of Pulmonary Embolism", Journal of the American College of Surgeons, 1999, 189:314-320.

Meissner, M.H. et al., Venous Thromoembolism in Trauma: A Local Manifestation of Systemic Hypercoagulability?, The Journal of Trauma: Injury, Infection, and Critical Care, Feb. 2003, vol. 54, No. 2, pp. 224-231.

Participants in the Vena Caval Filter Consensus Conference, "Recommended Reporting Standards For Vena Caval Filter Placement and Patient Follow-Up", Journal of Vascular and Interventional Radiology, 2003, 14:S427-S432.

Pelage, J. et al., "Re: Leiomyoma Recurrence After Uterine Artery Embolization", Journal of Vascular and Interventional Radiology, Jul. 2004, vol. 15, No. 7, pp. 773-776.

Quality Improvement Guidelines for Percutaneous Inferior Vena Cava Filter Placement For the Prevention of Pulmonary Embolism (European Standards adopted and Modified by CIRSE in Cooperation With SCVIR Standards of Practice Committee), http:www.cirse.org/vena_cava_filter_crise.htm, retrieved May 17, 2002, 11 pages.

RD Heparin Arthroplasty Group, "RD Heparin Compared With Warfarin For Prevention of Venous Thromboembolic Disease Following Total Hip or Knee Arthroplasty", The Journal of Bone and Joint Surgery, Incorporation, Aug. 1994, vol. 76-A, No. 8, pp. 1174-1185.

Adams, E. et al., "Retrievable Inferior Vena Cava Filter For Thrombolic Disease in Pregnancy", British Journal of Obstetrics and Gynaecology, Sep. 1998, vol. 105, pp. 1039-1042.

Authors' Abstract, "Abstracts of Current Literature", Journal of Vascular and Interventional Radiology, Mar. 2000, vol. 11, No. 3, pp. 402-407.

Consensus Conference, "Prevention of Venous Thrombosis and Pulmonary Embolism", JAMA, Aug. 8, 1986, vol. 256, No. 6, pp. 744-749.

Hirsch, D. R. et al., "Prevalence of Deep Venous Thrombosis Among Patients in Medical Intensive Care", JAMA, Jul. 26, 1995, 274(4):335337.

Hirsch, S. B. et al., Case Reports: Accidental Placement of the Greenfield Filter in the Heart: Report of Two Cases et al., Journal of Vascular Surgery, Dec. 1987, vol. 6, No. 6.

Hoff, W. S. et al., "Early Experience With Retrievable Inferior Vena Cava Filters in High-Risk Trauma Patients", Journal of the American College of Surgeons, Dec. 2004, vol. 199, No. 6, pp. 869-874.

Hyers, T. M. et al., "Antithrombotic Therapy For Venous Thromboembolic Disease", Chest, Jan. 2001, 119(1):176S-193S.

Ihnat, D. M. et al., "Treatment of Patients With Venous Thromboembolism and Malignant Disease: Should Vena Cava Filter Placement Be Routine?", Journal of Vascular Surgery, Nov. 1998, vol. 28, No. 8, pp. 800-807.

Inge, T. H. et al., "Bariatric Surgery for Severely Overweight Adolescents: Concerns and Recommendations", Pediatrics, Jul. 2004, vol. 114, No. 1, pp. 217-223.

Izutani, H. et al., "Migration of an Inferior Vena Cava Filter to the Right Ventricle and Literature Review", Can J Cardiol, Feb. 2004, vol. 20, No. 2, pp. 233-235.

Jacobs, D. G. et al., "The Role of Vena Caval Filters in the Management of Venous Thromboembolism" The American Surgeon, Aug. 2003, vol. 69, No. 8, pp. 635-642.

Jacobs, D. G. et al., Letters to the Editor, The Journal of Trauma, Dec. 1997, vol. 43, No. 6, pp. 988-989.

Jain, V. et al., "Preoperative Vena Caval Interruption for Venous Thrombosis Associated With Ovarian Malignancy", Acta Obstetricia Et Gynecologica Scandinavica.

Jarrett B.P. et al., Inferior Vena Cava Filters in Malignant Disease, Journal of Vascular Surgery, 2002, 36:704-707.

Joels, C. S. et al., "Complications of Inferior Vena Cava Filters", The American Surgeon, Aug. 2003, vol. 69, No. 8, pp. 654-659.

Jones K. V. et al., "Tricuspid Insufficiency After Intracardiac Migration of a Greenfield Filter: Case Report And Review of The Literature", Journal of Vascular Surgery, Sep. 1996, vol. 24, No. 3, pp. 494-498.

Kellum, J. M., "Gastric Banding" Annals of Surgery, Jan. 2003, vol. 237, No. 1, pp. 17-18.

Kelly, J. et al., "Anticoagulation or Inferior Vena Cava Filter Placement for Patients With Primary Intracerebral Hemorrhage Developing Venous Thromboembolism?", Stroke, 2003, 34:2999-3005.

Kerr, A. et al., "Bidirectional Vena Cava Filter Placement", Journal of Vascular Surgery, Oct. 1995, vol. 22, No. 4.

Khansarinia, S. et al., Prophylactic Greenfield Filter Placement in Selected High-Risk Trauma Patients, Journal of Vascular Surgery, 1995, 22:231-236.

Kim, D. et al., "Insertion of the Simon Nitinol Caval Filter: Value of the Antecubital Vein Approach", American Journal of Roentgenology, Sep. 1991, 157:521-522.

Kim, J. et al., "Preliminary Report on the Safety of Heparin for Deep Venous Thrombosis Prophylaxis After Severe Head Injury", The Journal of Trauma: Injury, Infection, and Critical Care, Jul. 2002, vol. 53, No. 1, pp. 38-43.

Kim, V. et al., "Epidemiology of Venous Thromboembolic Disease", Emergency Medicine Clinics of North America, Nov. 2001, vol. 19, No. 4, pp. 839-859.

Kimmerly, W. S. et al., "Graduate Surgical Trainee Attitudes Toward Postoperative Thromboprophylaxis", Southern Medical Journal, Aug. 1999, vol. 92, No. 9, pp. 790-794.

Kinney, T. B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.

Kinney, T. B. et al., "Regarding "Limb Asymmetry in Titanium Greenfield Filters: Clinically Significant?"", Journal of Vascular Surgery, Jun. 1998, vol. 27, No. 6.

Kistner, R. L., Definitive Diagnosis and Definitive Treatment in Chronic Venous Disease: A Concept Whose Time Has Come:, Journal of Vascular Surgery, Nov. 1996, vol. 24, No. 5, pp. 703-710.

Knudson, M. M. et al., "Prevention of Venous Thromboembolism in Trauma Patients", The Journal of Trauma, Sep. 1994, vol. 37, No. 3, pp. 480-487.

Knudson, M. M. et al., "Thromboembolism After Trauma-An Analysis of 1602 Episodes From the American College of Surgeons National Trauma Data Bank" Annals of Surgery, Sep. 2004, vol. 240, No. 3, pp. 490-498.

Knudson, M. M. et al., Thromboembolism Following Multiple Trauma, The Journal of Trauma, Jan. 1992, vol. 32, No. 1, pp. 2-11.

Knudson, M. M. et al., "Venous Thromboembolism After Trauma", Current Opinion in Critical Care, 2004, 10:539-548.

Koga, F. et al., "Deep Vein Thrombosis During Chemotherapy in a Patient With Advanced Testicular Cancer: Successful Percutaneous Thrombectomy Under Temperary Placement of Retrievable Inferior Vena Cava Filter", International Journal of Uroloty, 2001, 8:90-93.

Konya, A. et al., "New Embolization Coil Containing a Nitinol Wire Core: Preliminary in Vitro and in Vivo Experiences", Journal of Vascular and Interventional Radiology, 2001, 12:869-877.

Kreutzer J.et al., "Healing Response to the Clamshell Device For Closure of Intracardiac Defects in Humans", Catheterization and Cardiovascular Interventions, 2001, vol. 54.

Kudsk, K. A. et al., "Silent Deep Vein Thrombosis in Immobilized Multiple Trauma Patients", The American Journal of Surgery, Dec. 1989, vol. 158, pp. 515-519.

Kyrle, P. A. et al., Deep Vein Thrombosis, The Lancet, Mar. 26-Apr. 1, 2005, 365(9465):1163-1174.

Langan III, E. M. et al., "Prophylactic Inferior Vena Cava Filters in Trauma Patients at High Risk: Follow-Up Examination and Risk/Benefit Assessment", Journal of Vascular Surgery, 1999, 30:484-490.

Leach, T. A. et al., "Surgical Prophylaxis for Pulmonary Embolism", The American Surgeon, Apr. 1994, vol. 60, No. 4, pp. 292-295.

Leoni, C. J. et al., "Classifying Complications of Interventional Procedures: A Survey of Practicing Radiologists", Journal of Vascular and Interventional Radiology, 2001, 12:55-59.

Letai, A., "Cancer, Coagulation, and Anticoagulation", The Oncologist, 1999, 4:443-449.

Lewis-Carey, M. B. et al., "Temporary IVC Filtration Before Patent Foramen Ovale Closure in a Patient With Paradoxic Embolism", Journal of Vascular and Interventional Radiology, 2002, 13:1275-1278.

Lidagoster, M. I. et al., Superior Vena Cava Occlusion After Filter Insertion, Journal of Vascular Surgery, Jul. 1994, vol. 20, No. 1.

Lin, J. et al., "Factors Associated With Recurrent Venous Thromboembolism in Patients With Malignant Disease", Journal of Vascular Surgery, 2003, 37:976-983.

Lin, P. H. et al., "The Regained Referral Ground and Clinical Practice of Vena Cava Filter Placement in Vascular Surgery", The American Surgeon, Oct. 2002, vol. 68, No. 10, pp. 865-870.

Linsenmaier U. et al, "Indications, Management, and Complications of Temporary Inferior Vena Cava Filters", Cardiovascular and Interventional Radiology, 1998, 21:464-469.

Lopez-Beret, P. et al., "Systematic Study of Occult Pulmonary Thromboembolism in Patients With Deep Venous Thrombosis", Journal of Vascular Surgery, 2001, 33:515-521.

Lorch, H. et al., "In Vitro Studies of Temporary Vena Cava Filters", Cardiovascular and Interventional Radiology, 1998, 21:146-150.

Lujan, J. A. et al., "Laparoscopic Versus Open Gastric Bypass in the Treatment of Morbid Obesity", Annals of Surgery, Apr. 2004, vol. 239, No. 4, pp. 433-437.

Luo, X. Y. et al., "Non-Newtonian Flow Patterns Associated With an Arterial Stenosis", Journal of Biomechanical engineering, Nov. 1992, 114:512-514.

MacDonald, K. G. Jr., "Overview of the Epidemiology of Obesity and the Early History of Procedures to Remedy Morbid Obesity", Archives of Surgery, Apr. 2003, 138(4):357-360.

Manke, C. et al., "MR Imaging-Guided Stent Placement in Iliac Arterial Stenoses: A Feasibility Study", Radioilogy, 2001, 219:527-534.

Matthews, B. D. et al., "Inferior Vena Cava Filter Placement: Preinsertion Inferior Vena Cava Imaging", The American Surgeon, Aug. 2003, vol. 69, No. 8, pp. 649-653.

Mortele, K. J. et al., "The Swedish Laparoscopic Adjustable Gastric Banding for Morbid Obesity: Radiologic Findings in 218 Patients", American Journal of Roentgenology, 2001, 177:77-84.

Murakami, M. et al., "Deep Venous Thrombosis Prophylaxis in Trauma: Improved Compliance With a Novel Miniaturized Pneumatic Compression Device", Journal of Vascular Surgery, 2003, 38:923-927.

Nakagawa, N. et al., "A Retrievable Nitinol Vena Cava Filter: Experimental and Initial Clinical Results", Journal of Vascular and Interventional Radiology, 1994, 5:507-512.

Napolitano, L. M. et al., "Asymptomatic Deep Venous Thrombosis in the Trauma Patient: Is an Aggressive Screening Protocol Justified?", The Journal of Trauma: Injury, Infection, and Critical Care, 1997, vol. 39, No. 4, pp. 651-659.

Nazario, R. et al., "Treatment of Venous Thromboembolism", Cardiology in Review, 2002, 10(4):249-259.

Neeman, Z. et al., "Metastatic Involvement of a Retrieved Inferior Vena Cava Filter", (Clinical Center) and National Cancer Institute, National Institutes of Health, Bethesda, MD), p. 1585.

Neill, A. M. et al., "Retrievable Inferior Vena Caval Filter For Thromboembolic Disease in Pregnancy", British Journal of Obstetrics and Gynaecology, Dec. 1997, vol. 104, pp. 1416-1418.

Neri, E. et al., "Protected Iliofemoral Venous Thrombectomy in a Pregnant Woman With Pulmonary Embolism and Ischemic Venous Thrombosis", Texas Heart Institute Journal, 2002, vol. 29, No. 2, pp. 130-132.

Nguyen, N. T. et al., "A Comparison Study of Laparoscopic Versus Open Gastric Bypass for Morbid Obesity", Journal of the American College of Surgeons, Aug. 2000, vol. 191, No. 2, pp. 149-155.

Nguyen, N. T. et al., "Comparison of Pulmonary Function and Postoperative Pain After Laparoscopic Versus Open Gastric Bypass: A Randomized Trial", Journal of Americal College of Surgeons, 2001, 192:469-477.

Norwood, S. H. et al., "A Potentially Expanded Role For Enoxaparin in Preventing Venous Thromboembolism in High Risk Blunt Trauma Patients", Journal of the American College of Surgeons, 2001, 192:161-167.

Nunn, C. R. et al., Cost-Effective Method for Bedside Insertion of Vena Caval Filters in Trauma Patients, The Journal of Trauma, Nov. 1997, vol. 43, No. 5, pp. 752-758.

O'Brien, P. E. et al., "Laparoscopic Adjustable Gastric Banding in the Treatment of Morbid Obesity", Archives of Surgery, Apr. 2003, 138(4):376-382.

O'Malley, K. F. et al., "Prevention of Pulmonary Embolism After Pelvic Fracture: Rational Use of Inferior Vena Caval Filters", (Cooper Hospital/University Medical Center), Jan. 1996, vol. 40.

O'Sullivan, G. J. et al., "Endovascular Management of Iliac Vein Compression (May-Thurner) Syndrome", Journal of Vascular and Interventional Radiology, 2000, 11:823-836.

Offner, P. J. et al., "The Role of Temporary Inferior Vena Cava Filters in Critically Ill Surgical Patients", Archives of Surgery, Jun. 2003, vol. 138, pp. 591-595.

Olearchyk, A. S., "Insertion of the Inferior Vena Cava Filter Followed by Iliofemoral Venous Thrombectomy for Ischemic Venous Thrombosis", Journal of Vascular Surgery, Apr. 1987, vol. 5, No. 4, pp. 645-647.

Olin, J. W., "Pulmonary Embolism", Reviews in Cardiovascular Medicine, 2002, 3(2):S68-S75.

Ornstein, D. L. et al., "Cancer, Thrombosis, and Anticoagulants", Current Opinion in Pulmonary Medicine, 2000, 6:301-308.

Ortega, M. et al., "Efficacy of Anticoagulation Post-Inferior Vena Caval Filter Placement", American Surgeon, May 1998, vol. 64, Issue 5, pp. 419-423.

Ortiz-Saracho, J. et al., "An Unusual Cause of Pulmonary Artery Thrombosis", Chest, 1998, 114:309-310.

Owings, J. T. et al., "Timing of the Occurrence of Pulmonary Embolism in Trauma Patients", Archives of Surgery, Aug. 1997, 132(8):862-867.

Padberg, F. T. et al, "Hemodynamic and Clinical Improvement After Superficial Vein Ablation in Primary Combined Venous Insufficiency With Ulceration", Journal of Vascular Surgery, 1996, 24:711-718.

Pais, S. O. et al., "Percutaneous Insertion of the Greenfield Inferior Vena Cava Filter: Experience With Ninety-Six Patients", Journal of Vascular Surgery, Oct. 1988, vol. 8, No. 4.

Papers of the Western Surgical Association, "Directed Parathyroidectomy—Feasibility and Performance in 100 Consecutive Patients With Primary Hyperparathyroidism", Archives of Surgery, Jun. 2003, vol. 138, p. 637.

Participants in the Vena Caval Filter Consensus Conference, "Recommended Reporting Standards For Vena Caval Filter Placement and Patient Follow-Up", Journal of Vascular Surgery, 1999, 30:573-579.

Partsch, H. et al., "Frequency of Pulmonary Embolism in Patients Who Have Iliofemoral Deep Vein Thrombosis and Are Treated With Once- or Twice-Daily Low-Molecular Weight Heparin", Journal of Vascular Surgery, 1996, 24:774-782.

Passman, M. A. et al., "Pulmonary Embolism is Associated With the Combination of Isolated Calf Vein Thrombosis and Respitory Symptoms", Journal or Vascular Surgery, 1997, 25:39-45.

Patton, J. H. Jr., et al., "Prophylactic Greenfield Filters: Acute Complications and Long-Term Follow-Up", The Journal of Trauma: Injury, Infection, and Critical Care, 1996, vol. 41, No. 2, pp. 231-237.

Peck, K. E. et al., "Postlaparoscopic Traumatic Inferior Vena Caval Thrombosis", Heart & Lung, Jul./Aug. 1998, vol. 27, No. 4, pp. 279-281.

Peterson, D. A. et al., "Computed Tomographic Venography is Specific But Not Sensitive For Diagnosis of Acute Lower-Extremity Deep Venous Thrombosis in Patients With Suspected Pulmonary Embolus", Journal of Vascular Surgery, 2001, 34:798-804.

Podnos, Y. D. et al., "Complications After Laparoscopic Gastric Bypass", Archives of Surgery, Sep. 2003, 138:957-961.

Porter, J. M. et al., "Reporting Standards in Venous Disease: An Update", Journal of Vascular Surgery, 1995, 21:635-645.

Prince, M. R. et al., "The Diameter of the Inferior Vena Cava and Its Implications for the Use of Vena Caval Filters", Radiology, 1983, 149:687-689.

Proctor, M. C. et al., "Assessment of Apparent Vena Caval Penetration by the Greenfield Filter", Journal of Endovascualr Surgery, 1998, 5:251-258.

Proctor, M. C., "Indications for Filter Placement", Seminars in Vascular Surgery, Sep. 2000, vol. 13, No. 3, pp. 194-198.

Qanadli, S. D. et al., "Pulmonary Embolism Detection: Prospective Evaluation of Dual-Section Helical CT Versus Selective Pulmonary Arteriography in 157 Patients", Radiology, 2000, 217:447-455.

Quirke, T. E. et al., "Inferior Vena Caval Filter Use in U.S. Trauma Centers" A Practitioner Survey, The Journal of Trauma: Injury, Infection, and Critical Care, 1997, vol. 43, No. 2, pp. 333-337.

Rabkin, D. J. et al., "Nitinol Properties Affecting Uses in Interventional Radiology", Journal of Vascular and Interventional Radiology, 2000, 11:343-350.

Radke, P. W. et al., "Thrombosis in Behcet's Disease: Report of a Case Followed by a Systematic Review Using the Methodology of Evidence-Based Medicine", Journal of Thrombosis and Thrombolysis, Apr. 2001, 11(2):137-141.

Raju, N. L. et al., "Case 37: Juxtacaval Fat Collection-Mimic of Lipoma in the Subdiaphragmatic Inferior Vena Cava", Radiology, 2001, 220:471-474.

Rascona, D. A. et al., "Pulmonary Embolism-Treatment vs Nontreatment", Chest, Jun. 1999, vol. 115, No. 6, p. 1755.

Razavi, M. K. et al., "Chronically Occluded Inferior Venae Cavae: Endovascular Treatment", Radiology, 2000, 214:133-138.

Reddy, K. et al., "Insertion of an Inferior Venocaval Filter in a Pregnant Woman at Risk for Pulmonary Embolism-A Challenging Management", Departments of Obstetrics and Gynaecology and Radiology, Wexham Park Hospital, Slough, UK, 2003, p. 198.

Reekers, J. A. et al., "Evaluation of the Retrievability of the OptEase IVC Filter in an Animal Model", Journal of Vascular and Interventional Radiology, 2004, 15:261-267.

Ricotta, J. J., Regarding "Recurrent Thromboembolism in Patients With Vena Caval Filters", Journal of Vascular Surgery, 2001, vol. 33, p. 657.

Riedel, M., "Acute Pulmonary Embolism 2: Treatment", Heart, Mar. 2001, 85(3):351-360.

Robrer, M. J. et al., "Extended Indications For Placement of an Inferior Vena Cava Filter", Journal of Vascular Surgery, Jul. 1990, vol. 12, No. 1.

Rodrigues, H. L. et al., "Update of the Management of Venous Thromboembolism [16]", Rev Port Cardiol, 2002, 21(2):183-199.

Rodriguez, J. L. et al., "Early Placement of Prophylactic Vena Caval Filters in Injured Patients at High Risk for Pulmonary Embolism", The Journal of Trauma, Injury, Infection, and Critical Care, 1996, vol. 40, No. 5, pp. 797-804.

Ashley, D. W. et al., "Accurate Deployment of Vena Cava Fitters: Comparison of Intravascular Ultrasound and Contrast Venography", The Journal of Trauma: Injury, Infection, and Critical Care, Jun. 2001, vol. 50, No. 6, pp. 975-981.

Authors' Abstract, Journal of Vascular and Interventional Radiology, Oct. 2002, 13(10):1062-1068.

Critical Care Medicine, vol. 32, No. 12 (Suppl.), pp. A181-A188.

Doherty, C., "Special Problems of Massive Obesity", Primary Care Physician'S Resource Center, file://D:\Special%20Problems%20of%20Massive%20Massive%20Obesity.htm, retrieved Jul. 26, 2005.

Gosin, J. S., "Efficacy of Prophylactic Vena Cava Filters in High-Risk Trauma Patients", Annals of Vascular Surgery, 1997, 11:100-105.

Greenfield, L J., "Does Cervical Spinal Cord Injury Induce a Higher Incidence of Complications After Prophylactic Greenfield Filter Usage?", Journal of Vascular and Interventional Radiology, Jul.-Aug. 1997, pp. 719-720.

Ha, T. G. Van et al., "Removal of Gunther Tulip Vena Cava Filter Through Femoral Vein Approach", Journal of Vascular and Interventional Radiology, 2005, 16:391-394.

Letters to the Editor, Journal of the American College of Surgeons, Mar. 1996, vol. 182, pp. 279-280.

Miller, A. C., "British Thoracic Society Guidelines for the Management of Suspected Acute Pulmonary Embolism", Thorax, Jun. 2003, 58(6): 470-483.

Millward, S., "Temporary IVC Filtration Before Patent Foramen Ovale Closure in a Patient With Paradoxic Embolism", Letter to the Editor, p. 937.

Natta, T. L. Van et al., "Elective Bedside Surgery in Critically Injured Patients is Safe and Cost-Effective", Amercian Surgery, May 1998, 22(5):618-626.

Oppat, W. F. et al., "Intravascular Ultrasound-Guided Vena Cava Filter Placement", Journal of Endovascular Surgery, 1999, 6:285-287.

Participants in the Vena Caval Filter Consensus Conference, Recommended Reporting Standards for Vena Caval Filter Placement and Patient Follow-Up, Journal of Vascular Surgery, Sep. 1999, 30(3):573-579.

Poster: Clinical Science: Pulmonary Disease or Dysfunctional/Mechanical Ventilation/Weaning (Adult, Critical Care Medicine, vol. 32, No. 12 (Suppl.), pp. A111-A120.

Rogers, F. B. et al., "Five-Year Follow-Up of Prophylactic Vena Cava Filters in High-Risk Trauma Patients", Archives of Surgery, Apr. 1998, 133:406-411.

Rogers, F. B. et al., "Practice Management Guidelines for the Prevention of Venous Thromboembolism in Trauma Patients: The EAST Practice Management Guidelines Work Group", The Journal of Trauma: Injury, Infection, and Critical Care, Jul. 2002, 53:142-164.

Rogers, F. B. et al., "Prophylactic Vena Cava Filter Insertion in Severely Injured Trauma Patients: Indications and Preliminary Results", The Journal of Trauma, Oct. 1993, 35(4):637-642.

Rogers, F. B. et al., "Prophylactic Vena Cava Filter Insertion in Selected High-Risk Orthopaedic Trauma Patients", Journal of Orthopaedic Trauma, 1997, 11(4):267-272.

Rogers, F. B. et al., "Routine Prophylactic Vena Cava Filter Insertion in Severely Injured Trauma Patients Decreases the Incidence of Pulmonary Embolism", Journal of the American College of Surgeons, Jun. 1995 180(6):641-647.

Rogers, F. B., "Venous Thromboembolism in Trauma Patients: A Review", Surgery, Jul. 2001, vol. 130, No. 1, pp. 1-12.

Rohrer, M. J. et al., "Extended Indications For Placement of an Inferior Vena Cava Filter", Journal of Vascular Surgery, Jul. 1989, vol. 10. No. 1, pp. 44-50.

Rose, S. C. et al., "Placement of Inferior Vena Caval Filters in the Intensive Care Unit", Journal of Vascular and Interventional Radiology, 1997, 8:61-64.

Rose, S. C. et al., "Regarding "Bedside Vena Cava Filter Placement Guided With Intravascular Ultrasound"", Journal of Vascular Surgery, Apr. 2002, vol. 35, No. 4.

Rossi, G. et al., "Open To Critique: An Unusual Complication of Vena Cava Filter Placement", Journal of Vascular Surgery, Nov. 1996, vol. 24, No. 5.

Rubin, B. G. et al., "Care of Patients With Deep Venous Thrombosis in an Academic Medical Center: Limitations and Lessons", Journal of Vascular Surgery, 1994, 20:698-704.

Ruiz, A. J. et al., "Heparin, Deep Venous Thrombosis, and Trauma Patients", The American Journal of Surgery, Aug. 1991, 162:159-162.

Ryskamp, R. P. et al., "Utilization of Venous Thromboembolism Prophylaxis in a Medical-Surgical ICU", Chest, Jan. 1998, 113(1):162-164.

Sapala, J. A. et al., "Fatal Pulmonary Embolism After Bariatric Operations for Morbid Obesity: A 24-Year Retrospective Analysis", Obesity Surgery, 2003, 13:819-825.

Sarasin, F. P. et al., "Management and Prevention of Thromboemboli in Patients With Cancer-Related Hypercoagulable", Journal of General Internal Medicine, Sep. 1993, 8:476-485.

Schultz, D. J. et al., "Incidence of Asymptomatic Pulmonary Embolism in Moderately to Severely Injured Trauma Patients", Journal of Trauma: Injury, Infection, and Critical Care, 2004, 56:727-733.

Shackford, S. R. et al., "Venous Thromboembolism in Patients With Major Trauma", The American Journal of Surgery, Apr. 1990, vol. 1 59, pp. 365-369.

Shaer, J. et al., "An Unusual Cause of Low Back Pain?: A Case Report", Spine, Jun. 15, 1998, 23(12):1349-1350.

Sharpe, R. P. et al., "Incidence and Natural History of Below-Knee Deep Venous Thrombosis in High-Risk Trauma Patients", The Journal of Trauma: Injury, Infection, and Critical Care, Dec. 2002, 53:1048-1052.

Sheikh, M. A. et al., "Images in Vascular Medicine", Vascular Medicine 2001, 6:63-64.

Sheikh, M. A. et al., "Isolated Internal Jugular Vein Thrombosis: Risk Factors and Natural History", Vascular Medicine, 2002, 7:177-179.

Siddique, R. M. et al., "Thirty-Day Case-Fatality Rates for Pulmonary Embolism in the Elderly", Archives of Internal Medicine, Nov. 11, 1996, 156:2343-2347.

Simon, M. et al., "Comparative Evaluation of Clinically Available Inferior Vena Cava Filters With an In Vitro Physiologic Simulation of the Vena Cava", Radiology, 1993, 189:769-774.

Simon, M. et al., "Paddle-Wheel CT Display of Pulmonary Arteries and Other Lung Structures: A New Imaging Approach", American Journal of Roentgenology, Jul. 2001, pp. 195-198.

Simon, M., "Vena Cava Filters: Prevalent Misconceptions", Journal of Vascular and Interventional Radiology, 1999, 10:1021-1024.

Simon, M. et al., "A Vena Cava Filter Using Thermal Shape Memory Alloy", Radiology, Oct. 1977, 125:89-94.

Sing, R. F. et al., "Bedside Carbon Dioxide ($CO_2$) Preinsertion Cavagram for Inferior Vena Cava Filter Placement: Case Report", Journal of Trauma, Dec. 1999, 47(6):1140-1142.

Sing, R. F. et al., "Bedside Carbon Dioxide Cavagrams for Inferior Vena Cava Filters: Preliminary Results", Journal of Vascular Surgery, 2000, 32:144-147.

Sing, R. F. et al., "Bedside Insertion of Inferior Vena Cava Filters in the Intensive Care Unit", Journal of Trauma, Dec. 1999, 47(6):1104-1109.

Sing, R. F. et al., "Bedside Insertion of Inferior Vena Cava Filters in the Intensive Care Unit", Journal of American College of Surgeons, May 2001, 192(5):570-575.

Sing, R. F. et al., "Bedside Insertion of the Inferior Vena Cava Filter in the Intensive Care Unit", The American Surgeon, Aug. 2003, 69:660-662.

Sing, R. F. et al., "Guidewire Incidents With Inferior Vena Cava Filters", JAOA, Apr. 2001, 101(4):231-233.

Sing, R. F. et al., "Preliminary Results of Bedside Inferior Vena Cava Filter Placement", Chest, Jul. 1998, 114(1):315.

Sing, R. F. et al., Regarding "Bedside Vena Cava Filter Placement Guided With Intravascular Ultrasound", Journal of Vascular Surgery, May 2002, vol. 25, No. 5.

Smith, T. P. et al., "Acute Pulmonary Thromboembolism-Comparison of the Diagnostic Capabilities of Convention Film-Screen and Digital Angiography", Chest, 2002, 122:968-972.

Smith, T. P., "Pulmonary embolism: What's Wrong With This Diagnosis", American Journal of Roentgenology, Jun. 2000, 174:1489-1498.

Spain, D. A. et al., "Venous Thromboembolism in the High-Risk Trauma Patient: Do Risks Justify Aggressive Screening and Prophylaxis?", The Journal of Trauma: Injury, Infection, and Critical Care, 1997, vol. 42, No. 3, pp. 483-469.

Stavropoulos, S. W. et al., "In Vitro Study of Guide Wire Entrapment in Currently Available Inferior Vena Cava Filters", Journal of Vascular and Interventional Radiology, 2003, 14:905-910.

Stecker, M. S. et al., "Evaluation of a Spiral Nitinol Temporary Inferior Vena Caval Filter", Academic Radiology, 2001, 8:484-493.

Stein, P. D. et al., "Deep Venous Thrombosis in a General Hospital", Chest, 2002, 122:960-962.

Stein, P. D., "Opinions Regarding the Diagnosis and Management of Venous Thromboembolic Disease", Chest, Feb. 1998, vol. 113, No. 2, pp. 499-504.

Still, J. et al., "Experience With the Insertion of Vena Caval Filters in Acutely Burned Patients", The American Surgeon, Mar. 2000, vol. 66, No. 3, pp. 277-279.

Stover, M. D. et al., "Prospective Comparison of Contrast-Enhanced Computed Tomography Versus Magnetic Resonance Venography in the Detection of Occult Deep Pelvic Vein Thrombosis in Patients With Pelvic and Acetabular Fractures", Journal of Orthopaedic Trauma, 2002, 16(9):613-621.

Streib, E. W. et al., "Complications of Vascular Access Procedures in Patients With Vena Cava Filters", The Journal of Trauma: Injury Infection, and Critical Care, Sep. 2000, vol. 49, No. 3, pp. 553-558.

Sue, L. P. et al., "Iliofemoral Venous Injuries: An Indication For Prophylactic Caval Filter Placement", The Journal of Trauma: Injury, Infection, and Critical Care, 1995, vol. 39, No. 4, pp. 693-695.

Sugerman, H. J. et al., "Risks and Benefits of Gastric Bypass in Morbidity Obese Patients With Severe Venous Stasis Disease", Annals of Surgery, 2001, vol. 234, No. 1, pp. 41-46.

Sultan, S. et al., "Operative and Endovascular Management of Extracranial Vertebral Artery Aneurysm in Ehlers-Danlos Syndrome: A Clinical Dilemma", Vascular and Endovascular Surgery, 2002, 36(5):389-392.

Tai, N. R. M. et al., "Modern Management of Pulmonary Embolism", British Journal of Surgery, 1999, 86:853-868.

Thomas, J. H. et al., "Vena Caval Occlusion After Bird's Nest Filter Placement", American Journal of Surgery, Dec. 1998, vol. 176, pp. 598-600.

Thomas, L. A. et al., "Use of Greenfield Filters in Pregnant Women at Risk for Pulmonary Embolism", Southern Medical Journal, Feb. 1997, vol. 90, Issue 2.

Tillie-Leblond, I. et al., "Risk of Pulmonary Embolism After a Negative Spiral CT Angiogram in Patients With Pulmonary Disease: 1-Year Clinical Follow-Up Study", Radiology, 2002, 223:461-467.

Tips From Other Journals, American Family Physician, Feb. 1, 2003, vol. 67, No. 3, p. 593.

Tola, J. C. et al., "Bedside Placement of Inferior Vena Cava Filters in the Intensive Care Unit", The American Surgeon, Sep. 1999, vol. 65, No. 9, pp. 833-838.

Tovey, C. et al., "Diagnosis, Investigation, and Management of Deep Vein Thrombosis", British Medical Journal, May 31, 2003, vol. 326, i7400, p1180(5), 9 pages.

Trerotola, S. O. et al., "Preclinical in Vivo Testing of the Arrow-Trerotola Percutaneous Thrombolytic Device for Venous Thrombosis", Journal of Vascular and Interventional Radiology, 2001, 12:95-103.

Trujillo-Santos,J. et al., "Bed Rest or Ambulation in the Initial Treatment of Patients With Acute Deep Vein Thrombosis or Pulmonary Embolism", Chest, 2005, 127:1631-1636.

Tuna, I. C. et al., "Massive Pulmonary Embolus", Texas Heart Institute Journal, 2002, vol. 29, No. 2, pp. 144-145.

Urena, R. et al., "Bird's Nest Filter Migration to the Right Atrium", American Journal of Roentgenology, Oct. 2004, 183:1037-1039.

Valji, K., "Evolving Strategies for Thrombolytic Therapy of Peripheral Vascular Occlusion", Journal of Vascular and Interventional Radiology, 2000, 11:411-420.

Vedantham, S. et al., "Endovascular Recanalization of the Thrombosed Filter-Bearing Inferior Vena Cava", Journal of Vascular and Interventional Radiology, 2003, 14:893-903.

Vedantham, S. et al., "Lower Extremity Venous Thrombolysis With Adjunctive Mechanical Thrombectomy", Journal of Vascular and Interventional Radiology, 2002, 13:1001-1008.

Vedantham, S. et al., "Pharmacomechanical Thrombolysis and Early Stent Placement for Iliofemoral Deep Vein Thrombosis", Journal of Vascular and Interventional Radiology, 2004, 15:565-574.

Velmahos, G. C. et al., "Inability of an Aggressive Policy of Thromboprophylaxis to Prevent Deep Venous Thrombosis (DVT) in Critically Injured Patients: Are Current Methods of DVT Prophylaxis Insufficient?", Journal of the American College of Surgeons, 1998, 187:529-533.

Velmahos, G. C. et al., "Prevention of Venous Thromboembolism After Injury: An Evidence-Based Report-Part 1: Analysis of Risk Factors and Evaluation of the Role of Vena Caval Filters", The Journal of Trauma: Injury, Infection, and Critical Care, Jul. 2000, 49:132-139.

Velmahos, G. C. et al., "Prevention of Venous Thromboembolism After Injury: An Evidence-Based Report-Part II: Analysis of Risk Factors and Evaluation of the Role of Vena Caval Filters", The Journal of Trauma: Injury, Infection, and Critical Care, Jul. 2000, 49:140-144.

Velmahos, G. C. et al., "Spiral Computed Tomography for the Diagnosis of Pulmonary Embolism in Critically Ill Surgical Patients", Archives of Surgery, May 2001, 136(5):505-511.

Venbrux, Anthony C., "Protection Against Pulmonary Embolism: Permanent and Temporary Caval Filters" Department of Radiology-CVDL, The Johns Hopkins Medical Institutions, Baltimore MD, 7 pages.

Vesely, T. M. et al., "Preliminary Investigation of the Irie Inferior Vena Caval Filter", Journal of Vascular and Interventional Radiology, 1996,7:529-535.

Vorwerk, D. et al., "Use of a Temporary Caval Filter to Assist Percutaneous Iliocaval Thrombectomy: Experimental Results", Journal of Vascular and Interventional Radiology, Sep.-Oct. 1995, 6(5):737-740.

Vrachliotis, T. G. et al., "Percutaneous Management of Extensive Clot Trapped in a Temporary Vena Cava Filter", Journal of Endovascular Therapy, 2003, 10:1001-1005.

Wakefield, T. W., Treatment Options for Venous Thrombosis, Journal of Vascular Surgery, Mar. 2000, 31(3):613-620.

Wallace, M. J., "Transatrial Stent Placement for Treatment of Inferior Vena Cava Obstruction Secondary to Extension of Intracardiac Tumor Thrombus From Hepatocellular Carcinoma", Journal of Vascular Interventional Radiology, 2003, 14:1339-1343.

Wang, W. Y. et al., "Use of a Nitinol Gooseneck Snare to Open an Incompletely Expanded Over-the-Wire Stainless Steel Greenfield Filter", American Journal of Roentgenology, Feb. 1999, 172:499-500.

Watanabe, N. et al., "Images in Cardiology: Large Thrombus Entrapped in a Patent Foramen Ovale of the Atrial Septum, Which Apparently "Disappeared" Without Embolic Events", Heart, Nov. 2002, 88(5):474.

Watanabe, S. et al., "Superior Vena Caval Placement of a Temporary Filter: A Case Report",Vascular Surgery, Jan./Feb. 2001, vol. 35, Issue 1.

Welch, H. J. et al., "Duplex Assessment of Venous Reflux and Chronic Venous Insufficiency: The Significance of Deep Venous Reflux", Journal of Vascular Surgery, 1996, 24:755-762.

Wellons, E. D. et al., "Bedside Intravascular Ultrasound-Guided Vena Cava Filter Placement", Journal of Vascular Surgery, 2003, 38:455-458.

Wells, J. L. et al., "Diagnosing Pulmonary Embolism: A Medical Masquerader", Clinician Reviews, 2001, 11(2):66-79.

Westling, A. et al., "Incidence of Deep Venous Thrombosis in Patients Undergoing Obesity Surgery", World Journal of Surgery, 2002, 26:470-473.

White, R. H. et al., "A Population-Based Study of the Effectiveness of Inferior Vena Cava Filter Use Among Patients With Venous Thromboembolism", Archives of Internal Medicine, Jul. 10, 2000, 160(13):2033-2041.

Whitehill, T. A., "Current Vena Cava Filter Devices and Results", Seminars in Vascular Surgery, Sep. 2000, 13(3):204-212.

Wholey, M. et al., "Technique for Retrieval of a Guidewire Lodged in a Vena Cava Filter", Vascular and Endovascular Surgery, 2002, 36(5):385-387.

Wiles, C. E., Letters To Editor, Journal of Trauma, Aug. 1999, 47(2):438.

Wilson, J. T. et al., "Prophylactic Vena Cava Filter Insertion in Patients With Traumatic Spinal Cord Injury: Preliminary Results", Neurosurgery, 1994, 35:234-239.

Winchell, R. J. et al., "Risk Factors Associated With Pulmonary Embolism Despite Routine Prophylaxis: Implications For Improved Protection", The Journal of Trauma, 1994, 37(4):600-606.

Wittenberg, G. et al., "Long-Term Results of Vena Cava Filters: Experiences With the LGM and the Titanium Greenfield Devices", Cardiovascular and Interventional Radiology, 1998, 21:225-229.

Wittich, G. R. et al., "Anchoring a Migrating Inferior Vena Cava Stent With Use of a T-Fastener", Journal of Vascular and Interventional Radiology, 2001, 12:994-996.

Wojcik, R. et al., "Long-Term Follow-Up of Trauma Patients With a Vena Caval Fitter, The Journal of Trauma: Injury, Infection, and Critical Care", Nov. 2000, 49(5):839-843.

Wojtowycz, M. M. et al., "The Bird's Nest Inferior Vena Caval Filter: Review of a Single-Center Experience", Journal of Vascular and Interventional Radiology, 1997, 8:171-179.

Woodward, E. B. et al., "Delayed Retroperitoneal Arterial Hemorrhage After Inferior Vena Cava (IVC) Filter Insertion: Case Report and Literature Review of Caval Perforations by IVC Filters", Annals of Vascular Surgery, 2002, 16:193-196.

Xian, Z. Y. et al., "Multiple Emboli and Filter Function: An In Vitro Comparison of Three Vena Cava Filters", Journal of Vascular and Interventional Radiology, 1995, 6:887-893.

Xu, X. Y. et al., "Flow Studies in Canine Artery Bifurcations Using a Numerical Simulation Method", Journal of Biochemical Engineering, Nov. 1992, 114:504-511.

Yagi, A. et al., "Pulmonary Thromboembolism Evaluating the Indication and Effect of a Vena Caval Filter With Indium-111-Platelet Scintigraphy", Circulation Journal, Jun. 2004, 68:599-601.

Yonezawa, K. et al., "Effectiveness of an Inferior Vena Cava Filter as a Preventive Measure Against Pulmonary Thromboembolism After Abdominal Surgery", Surgery Today, 1999, 29:821-824.

Yucel, E. Kent, "Pulmonary MR Angiography: Is It Ready Now?", Radiology, 1999, 210:301-303.

Zamora, C. A. et al., "Prophylactic Stenting of the Inferior Vena Cava Before Transcatheter Embolization of Renal Cell Carcinomas: An Alternative to Filter Placement", Journal of Endovascular Therapy, 2004, 11:84-88.

Zanchetta, M. et al., "A New Permanent and Retrievable Vena Cava Filter: Its Removal After Five Months", Italian Heart Journal, Sep. 2001, 2(9):715-716.

Zeni, P. T. et al., "Use of Rheolytic Thrombectomy in Treatment of Acute Massive Pulmonary Embolism", Journal of Vascular and Interventional Radiology, 2003, 14:1511-1515.

Zinzindohoue, F. et al., "Laparoscopic Gastric Banding: A Minimally Invasive Surgical Treatment for Morbid Obesity-Prospective Study of 500 Consecutive Patients", Annals of Surgery, 2003,237(1):1-9.

* cited by examiner

NON-ENTANGLING VENA CAVA FILTER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

A vena cava filter is a device inserted into a blood vessel to capture particles in the blood flow. Typically the device is inserted into a major vein to prevent a blood clot from reaching the lungs. Patients who have recently suffered from trauma, heart attack (myocardial infarction), or underwent major surgical procedure (e.g., surgical repair of a fractured hip, etc.) may have thrombosis in a deep vein. When the thrombus clot loosens from the site of formation and travels to the lung it may cause pulmonary embolism, a life-threatening condition. A vena cava filter may be placed in the circulatory system to intercept the thrombi and prevent them from entering the lungs.

Examples of various blood vessel filters are disclosed in U.S. Patent Application, Publication No. 2001/0000799 A1, titled "BODY VESSEL FILTER" by Wessman et al., published May 3, 2001; U.S. Patent Application, Publication No. 2002/0038097 A1, titled "ATRAUMATIC ANCHORING AND DISENGAGEMENT MECHANISM FOR PERMANENT IMPLANT DEVICE" by Ostrovsky et al., published Sep. 26, 2002; U.S. Patent Application, Publication No. 2002/0193828 A1, titled "ENDOVASCULAR FILTER" by Griffin et al., published Dec. 19, 2002; U.S. Patent Application, Publication No. 2003/0199918 A1, titled "CONVERTIBLE BLOOD CLOT FILTER" by Patel et al., published Oct. 23, 2003; U.S. Patent Application, Publication No. 2003/0208227 A1, titled "TEMPORARY VASCULAR FILTERS AND METHODS" by Thomas, published Nov. 6, 2003; U.S. Patent Application, Publication No. 2003/0208253 A1, titled "BLOOD CLOT FILTER" by Beyer et al., published Nov. 6, 2003; U.S. Pat. No. 4,425,908, titled "BLOOD CLOT FILTER" issued to Simon, dated Jan. 17, 1984; U.S. Pat. No. 4,643,184, titled "EMBOLUS TRAP" issued to Mobin-Uddin, dated Feb. 17, 1987; U.S. Pat. No. 4,817,600, titled "IMPLANTABLE FILTER" issued to Herms et al., dated Apr. 4, 1989; U.S. Pat. No. 5,059,205, titled "PERCUTANEOUS ANTI-MIGRATION VENA CAVA FILTER" issued to El-Nounou et al., dated Oct. 22, 1991; U.S. Pat. No. 5,626,605, entitled "THROMBOSIS FILTER" issued to Irie et al., dated May 6, 1997; U.S. Pat. No. 5,755,790, titled "INTRALUMINAL MEDICAL DEVICE" issued to Chevillon et al., dated May 26, 1998; U.S. Pat. No. 6,258,026 B1, titled "REMOVABLE EMBOLUS BLOOD CLOT FILTER AND FILTER DELIVERY UNIT" issued to Ravenscroft et al., dated Jul. 10, 2001; U.S. Pat. No. 6,497,709 B1, titled "METAL MEDICAL DEVICE" issued to Heath, dated Dec. 24, 2002; U.S. Pat. No. 6,506,205 B2, titled "BLOOD CLOT FILTERING SYSTEM issued to Goldberg et al., dated Jan. 14, 2003; and U.S. Pat. No. 6,517,559 B1, titled "BLOOD FILTER AND METHOD FOR TREATING VASCULAR DISEASE" issued to O'Connell, dated Feb. 11, 2003; U.S. Pat. No. 6,540,767 B1, titled "RECOILABLE THROMBOSIS FILTERING DEVICE AND METHOD" issued to Walak et al., dated Apr. 1, 2003; U.S. Pat. No. 6,620,183 B2, titled "THROMBUS FILTER WITH BREAK-AWAY ANCHOR MEMBERS" issued to DiMatteo, dated Sep. 16, 2003; each of which is incorporated herein by reference in its entirety.

Typically the filter comprises a plurality of radially expandable legs that supports one or more filter baskets which are conical in configuration. The device is adapted for compression into a small size to facilitate delivery into a vascular passageway and is subsequently expandable into contact with the inner wall of the vessel. The device may later be retrieved from the deployed site by compressing the radially expanded legs and the associated baskets back into a small size for retrieval. The radially expandable leg may further comprise engagements for anchoring the filter in position within a blood vessel (e.g., vena cava). For example, the expandable legs may have hooks that can penetrate into the vessel wall and positively prevent migration of the filter in either direction along the length of the vessel. The body of the filter may comprise various biocompatible materials including compressible spring metals and shape memory materials to allow easy expansion and compression of the filter within the vessel. The hooks on the radially expandable legs may further comprise materials more elastic than the legs to permit the hooks to straighten in response to withdrawal forces to facilitate withdrawal from the endothelium layer without risk of significant injury to the vessel wall. In one variation, the hooks are formed on the ends of a portion of the radially expandable legs, but not on others.

Many of the existing vena cava filters routinely encounter problems during deployment due to entanglements of the radially expandable legs. This is especially problematic in designs with hooks implemented on the radially expandable legs. In the compressed/collapsed condition, the various hooks on the legs may interlock with other legs or hooks and render the device useless. Thus, an improved filter design that can prevent entanglement and/or interlocking of the radially expandable legs may be desirable. Such a design may improve the reliability of the vena cava filter and improve the surgical success rate of filter implantation. Such an improved design may also prevent the entanglement of the radially expandable legs when the device is collapsed into the compressed position during the retrieval of the filter from its deployed location within the vessel.

BRIEF SUMMARY OF THE INVENTION

Accordingly, described herein is an implantable vessel filter with a center-post configured to prevent entanglement of the filter's radially expandable legs. This improved vessel filter may prevent the radially expandable legs from entanglement and may further prevent the hooks on the radially expandable legs from interlocking. In one variation, the implantable vessel filter comprises a plurality of radially expandable elongated legs forming at least one conical-shaped filter when placed in the expanded position. A center-post is provided along the longitudinal axis of the filter to prevent the legs from entangling when the legs are collapsed inward toward the longitudinal axis of the filter. The center-post is configured to separate the legs and/or the associated hooks in the collapsed position. Surface profiles such as grooves or ledges may be provided on the center-post to separate the legs and/or hooks from each other. In one particular design, the distal portion of the center-post is configured with a plurality of cavities on the circumferential surface for receiving the hooks located at the proximal end of the radially expandable legs.

In another variation, the implantable vessel filter comprises a sleeve at the proximal end of the device and a plurality of elongated legs extending from the sleeve towards the distal direction. The legs are radially expandable. In the expanded position, a first set of the legs forms a first conical-shaped filter basket, and a second set of the legs forms a second conical-shaped filter basket distal to the first basket. As least three of the legs from the second set of the legs have hooks on them for anchoring into the vessel wall. Preferably, the hooks are located at the distal end of the legs. The implantable vessel filter further comprises a center-post connected to the sleeve and positioned along the longitudinal axis of the filter. The center-post is configured to prevent the legs from crossing the longitudinal axis so that the various legs do not entangle with each other and the hooks do not interlock. Preferably, grooves are provided on the circumferential surface of the center-post to further maintain the separation of the hooks when the legs are placed in the compressed position.

The improved implantable vessel filter may provide one or more of the various advantages listed below: improved loading into the delivery system; improved deployability due to easier release of the radially expandable legs; improved retrievability due to prevention of leg entanglement when the legs are collapsed inward for removal from the deployed site; trapping of significant emboli; good vessel patency and limited thrombogenic response at the implantation site; minimal migration along the length of the vessel after implantation; no perforation of the vessel wall; low profile for easy insertion; high durability, fatigue resistance and biocompatibility.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, tubing introducers or other filter deployment devices for implantation and/or retrieval of the filter in a vessel within a patient's body.

A vena cava filter is used herein as an example application of the filter device to illustrate the various aspects of the invention disclosed herein. In light of the disclosure herein, one of ordinary skill in the art would appreciate that variations of the filter device may be applicable for placement in various blood vessels, hollow body organs or elongated cavities in a human body for capturing particles in a fluid stream. It is also contemplated that the filter device described herein may be implemented for capturing particles other than blood clots.

It must also be noted that, as used in this specification and the appended claims, the singular forms "a," "an" and "the" include plural referents unless the context clearly dictates otherwise. Thus, for example, the term "a hook" is intended to mean a single hook or a combination of hooks, "a fluid" is intended to mean one or more fluids, or a mixture thereof.

Figure 1A:
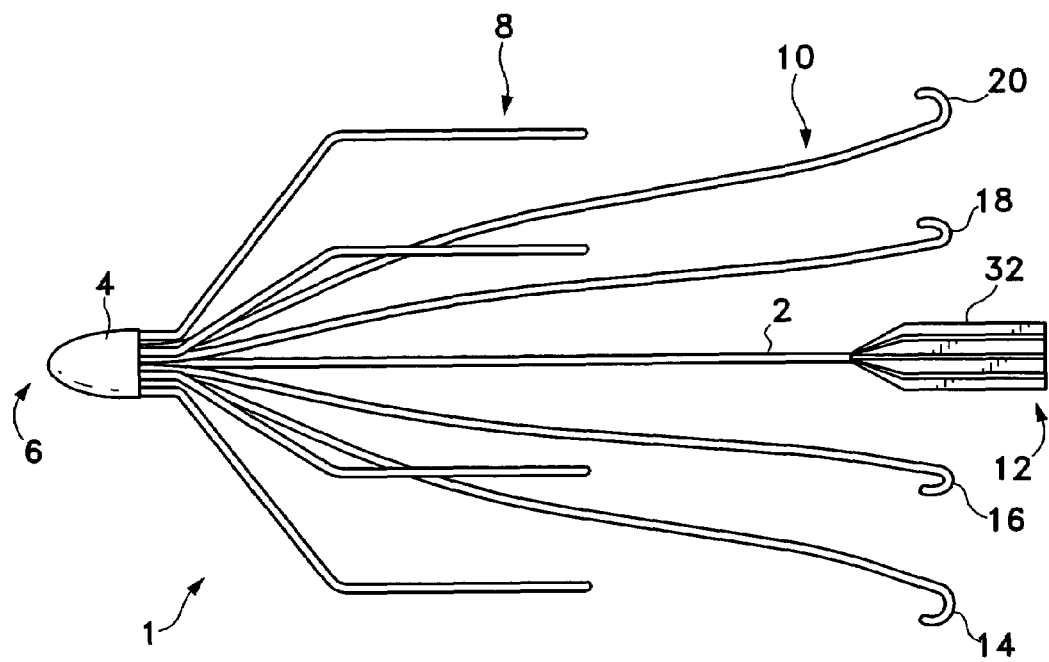
FIG. 1A illustrates one variation of an implantable vessel filter with a center-post for preventing entanglements of the radially expandable legs.
Figure 1B:
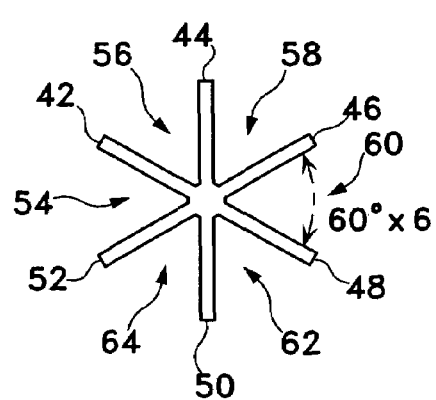
FIG. 1B shows the top view of the center-post of the implantable vessel filter of FIG. 1A. Flanges are provided at the distal end of the center-post, protruding in the radial direction, for separating the hooks at the distal end of the radially expandable legs.
Figure 1C:
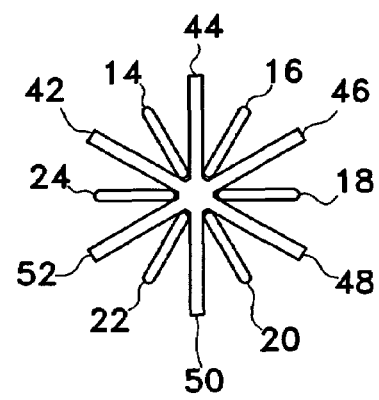
FIG. 1C is a diagram illustrating the placement of the hooks in between the flanges at the distal end of the center-post. In this particular variation, the height of the hooks is less than the height of the flanges in the radial direction from the center of the post, such that the flanges may prevent the hooks from tearing the inner walls of the vessel in the compressed position.

In one aspect of the invention, the implantable vessel filter 1 comprises an elongated body acting as the center-post 2 of the device, as shown in FIG. 1A. A sleeve 4 is connected to the proximal end of the center-post. The proximal end 6 of the sleeve 4 may be tapered to provide a bullet-shaped profile to facilitate the insertion and/or retrieval of the device in a vessel. A plurality of legs 8, 10 (e.g., flexible or semi-flexible wiring, etc.) extending from the sleeve 4 in the radial direction towards the distal end 12 of the device. The legs 8, 10 are configured with materials such that they may be collapsed toward the center-post 2 and positioned along the length of the center-post 2 for insertion and/or retrieval from a patient's vascular system. The plurality of legs comprises two sets of legs 8, 10. A first set of six legs 8, when expanded, forms a first conical-shaped filter basket centered around the center-post 2, which is on the longitudinal axis of the device 1. A second set of six legs 10, when expanded, forms a second conical-shaped filter basket positioned distal to the first basket, which is also centered around the center-post 2. Hooks 14, 16, 18, 20 are provided at the distal ends of the second set of legs 10 for anchoring the distal end of the second set of legs 10 into the walls of the vessel. An attachment 32 is provided at the distal end of the device for separating the hooks and preventing the hooks from interlocking with each other. Optionally, the attachment 32 comprises a plurality of flanges protruding in the radial direction from the center-post. In one design variation, the flanges 42, 44, 46, 48, 50, 52 are spaced equally around the circumferential surface of the attachment with spacing approximately 60 degrees apart, as shown in FIG. 1B. Each of the slots 54, 56, 58, 60, 62, 64 between the flanges 42, 44, 46, 48, 50, 52 may be configured to receive one hook. The height of the flanges 42, 44, 46, 48, 50, 52 may be configured to be greater than the height of the hooks 14, 16, 18, 20, 22, 24 in the radial direction, such that the tip of the hooks does not extend beyond the flanges when placed in the compressed position, as illustrated in FIG. 1C. This may prevent the tip of the hooks from accidentally tearing the wall of the vessel and allow smoother deployment and/or retrieval of the implantable vessel filter device.

In addition, the distal end of the center-post may be configured for attachment to a deployment device (e.g., introducer). For example, interlocking mechanisms matching the adaptor at an end of a deployment device may be provided to secure the implantable vessel filter to the tip of the deployment device for delivery and/or deployment. In another variation, the attachment positioned at the distal end of the center-post may be configured to serve dual functions such that the circumferential surface along the length of the attachment is configured with grooves for receiving and separating the hooks, while the distal end of the attachment is configured for interfacing with a deployment device. The grooves may be configured as indentations, cavities, raised surface profiles such as flanges, and other changes in surface profile. Alternatively, the proximal end of the attachment may be configured with an interface (e.g., hook, loop, etc.) for interconnecting with a deployment device to facilitate deployment and/or retrieval of the implantable vessel filter. In another variation, the device is configured such that in the compressed position the center-post extends distally beyond the length of the legs. At the distal end of the extended center-post, one may provide an interface or interlocking mechanism (e.g., hook, loop, etc.) for interconnecting with a deployment/retrieval device.

In yet another design variation, the center-post extends beyond proximal end of the sleeve and protrudes at the proximal end of the filter. The proximal end of the center-post may be configured with an interface or interlocking mechanism (e.g. hook, loop, etc.) for interconnecting with a filter deployment/retrieval device to facilitate deployment and/or retrieval of the implantable vessel filter.

Although in the example discuss above, the plurality of legs forms two filter baskets along the longitudinal length of the device. One may configure the device with only one filter basket, or alternatively with three or more filter baskets. In addition, the device may be configured with three or more legs forming each basket and is not limited to the six-legged basket as shown above. Also discussed earlier, barb feet (e.g., hooks) may be provided on the distal end of each leg. As one of ordinary skill in the art would appreciate, the precise length and angle of the barb feet may be designed to provide secure attachment to the vessel wall without causing perforation or tearing. Moreover, hooks may be provided on all the distal legs or only on some of the distal legs. Hooks may also be provided on the proximal legs if desired. Furthermore, secondary struts may be provided for interconnecting two or more of the radially expandable legs. The secondary struts may increase wiring density for each filter basket, which may in turn increase the filters capability to capture smaller particles.

The sleeve may be comprised of biocompatible metal, metal alloyed, or polymeric materials. The legs may be comprised of metal (e.g., stainless steel, titanium, etc.), metal alloyed (e.g., titanium alloy, elgiloy, an alloy comprises Cobalt-Nickel-Chromium, etc.), shape memory material (e.g., Nitinol), or polymeric materials (e.g., biocompatible plastics, etc.). The center-post may be comprised of metal, metal alloyed, polymeric materials or a combination thereof. For example, the center-post may be comprised of a metal alloyed core with polymeric coating on the outside. The grooves on the center-post for receiving the legs and/or the hooks may be an integral part of the shaft of the center-post, or they may be provided through an attachment connected to the center-post. The attachment may be comprised of metal, metal alloyed, polymeric material or a combination thereof.

Figure 2:
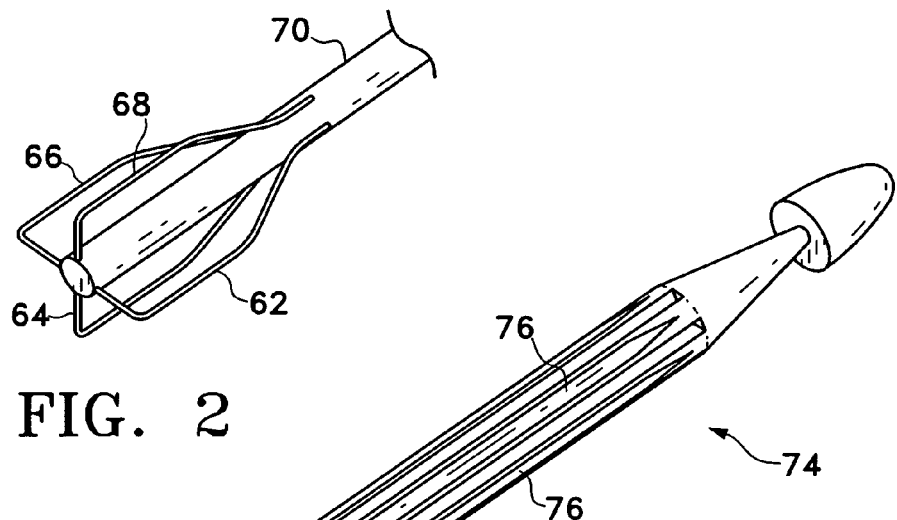
FIG. 2 illustrates another variation of the device where the wirings extending from the center-post provide the medium for separating the legs of the implantable vessel filter.
Figure 3:
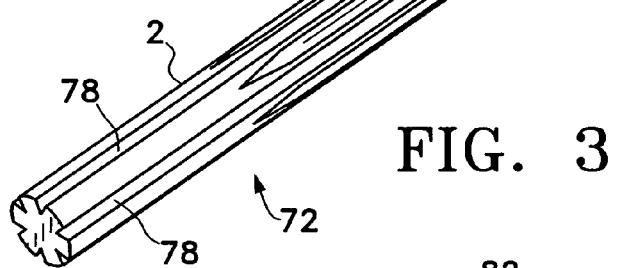
FIG. 3 illustrates yet another variation where the center-post has embedded grooves for receiving the radially expandable legs of the implantable vessel filter. In this variation, two sets of grooves are provided, with one set of grooves for receiving a first set of legs which forms the proximal filter basket, and a second set of grooves for receiving a second set of legs which forms the distal filter basket. The corresponding radially expandable legs are omitted in this particular figure.

In another variation, as shown in FIG. 2, the flanges 62, 64, 66, 68 at the distal portion of the center-post comprise wirings extending from the shaft 70 of the center-post. The looped wiring provides the medium to separate the hooks, while allowing fluid to flow through the center of the loops to minimize disruption of blood flow along the length of the device. In yet another variation, grooves or cavities are provided along the shaft of the center-post 2 for receiving the legs and/or the hooks. In one design, grooves are provided at the distal portion 72 of the shaft to receive the distal legs, with a hook at the distal end of each distal leg. In another design, the grooves are provided to receive all the legs of the device. In one variation, shown in FIG. 3, a first set of grooves 76 positioned along a proximal portion 74 of the shaft of the center-post 2 is provided to receive a first set of legs which forms a proximal filter basket, and a second set of grooves 78 positioned along the length of the shaft is provided to receive a second set of legs which form the distal filter basket. In FIG. 3, the filter device is shown without its corresponding radially expandable legs.

Figure 4:
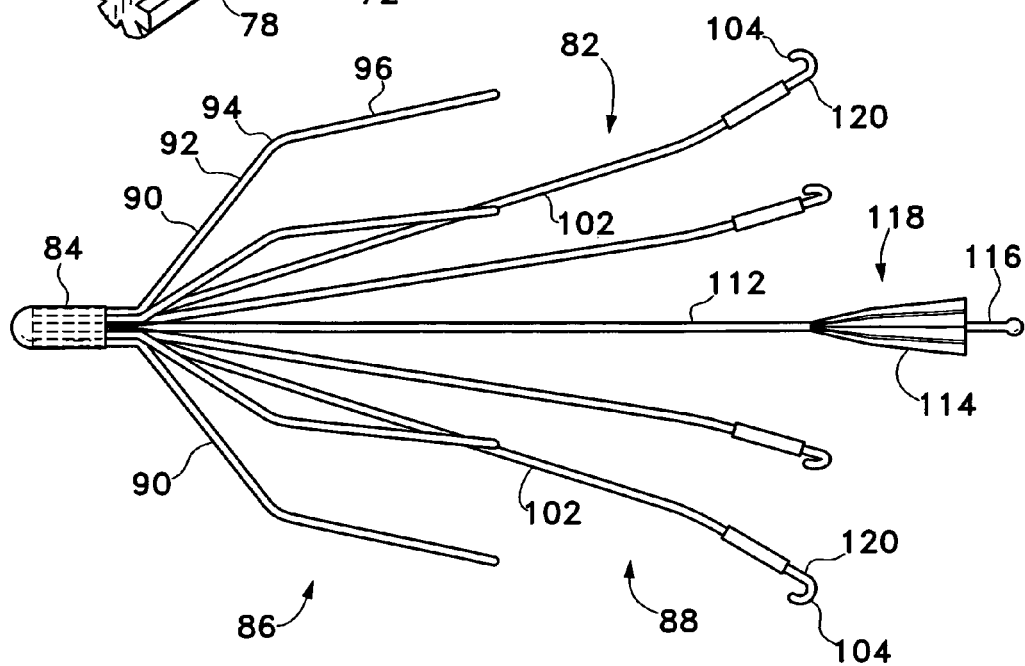
FIG. 4 is a diagrammatic view of another variation of an implantable vessel filter.

Referring now to FIG. 4, an expanded implantable vessel filter 82 is illustrated which is made from sets of elongate metal wires. In this variation, the wires are held together at the filter's proximal end by a hub 84 where they are plasma welded together to the hub or otherwise joined. In the low temperature martensite phase of wires made of thermal shape memory material (e.g., Nitinol alloy), the sets of wires can be straightened and held in a straight form that can pass through a length of fine plastic tubing with an internal diameter of approximately 2 mm (e.g., 8 French catheter). In its high temperature austenitic form, the vessel filter 82 recovers a preformed filtering shape as illustrated by FIG. 4. Similarly, wires of spring metal can be straightened and compressed within a catheter or tube and will diverge into the filter shape of FIG. 4 when the tube is removed.

In its normal expanded configuration or preformed filtering shape, the vessel filter 82 comprises a double filter, having a first proximally positioned basket section 86 and a second distally disposed filter basket section 88. The two filter basket sections provide peripheral portions which can both engage the inner wall of a body vessel at two longitudinally spaced locations, and the two filter basket sections are generally symmetrical about a longitudinal axis passing through the hub 84. On the other hand, the first filter basket section 86, which may act as a centering unit, may not always touch the vessel wall on all sides.

The first filter basket section 86 is formed from short lengths of wire, which form legs 90 that extend angularly, outwardly and then downwardly away from the hub 84 and towards the distal end of the vessel filter 82. Each leg 90 has a first leg section 92 which extends angularly outwardly from the hub 84 to a transition section 94, and an outer leg section 92 extends angularly from the transition section 94 toward the distal direction of the filter. The outer leg sections 96 are substantially straight lengths with ends which lie on a circle at their maximum divergence and engage the wall of a vessel at a slight angle (preferably within a range of from ten to forty-five degrees) to center the hub 84 within the vessel. For a filter which is to be removed by grasping the hub 84, it may be important for the hub to be centered. The filter may be configured with six wires 90 of equal length extending radially outward from the hub 84 and circumferentially spaced, such as, for example, by sixty degrees of arc.

The second filter basket section 88 is the primary filter and can include up to twelve circumferentially spaced straight wires 102 forming downwardly extending legs which tilt outwardly of the longitudinal axis of the filter 82 from the hub 84. A filter with a six wire configuration is discussed in this example, and the wires are of equal length. Alternatively, the length of the wiring may be staggered. The wires 102 are preferably much longer than the wires 90, and have distal tip sections which are uniquely formed, outwardly oriented hooks 104 which lie on a circle at the maximum divergence of the wires 102. There may be from three to twelve wires 102 formed with hooks 104, and in some instances, the wire legs 90 may include similarly formed hooks at the free ends thereof. The wires 102, in their expanded configuration of FIG. 4, are at a slight angle to the vessel wall, preferably within a range of from ten to forty-five degrees, while the hooks 104 penetrate the vessel wall to anchor the filter against movement. The wires 102 are radially offset relative to the wires 90 and may be positioned halfway between the wires 90 and also may be circumferentially spaced by sixty degrees of arc. Thus, the combined filter basket sections 86 and 88 can provide a wire positioned at every thirty degrees of arc at the maximum divergence of the filter sections. The filter section 88 forms a concave filter basket opening toward the distal end of the filter 82 while the filter section 86 forms a concave filter proximal of the filter section 88.

The vessel filter further comprises a center-post 112 positioned along the longitudinal axis of the filter with the proximal end of the center-post 112 connected to the hub 84. At the distal portion of the center-post, a raised surface profile 114 provides grooves for receiving the hooks 104 on the distal end of the distal legs 102. Preferably, each of the hooks 104 is provided with a corresponding groove on the shaft of the center-post 112. Alternatively, the grooves may be proved on the shaft to receive a portion of the distal leg 102 instead of the hook 104, thereby keeping the distal legs 102 from entangling with each other. In addition, the center-post 112 may have distal section 116 extending beyond the hook interface region 118. The extended distal section 116 may be configured to facilitate the handling of the vessel filter for pre-deployment preparation, deployment or extraction.

Furthermore, the hooks 114 on the distal legs may be further configured such that withdrawal force to which the hook is subjected will cause flexure in the juncture sections 120 so that the hook extends in the distal direction of the filter to a position parallel or semi-parallel with the axis of the leg 102. For example, the juncture section 120 may have considerably reduced cross-section relative to the cross-section of the leg 102 and the remainder of the hook 104 so that the stress exerted by the withdrawal tension may force it to bend outward. With the hook so straightened, it can be withdrawn without tearing the vessel wall, leaving only a small puncture. In an alternative design, the entire hook 104 can be formed with a cross-section throughout its length which is less than that of the leg 102. This may result in straightening of the hook over its entire length in response to a withdrawal force. This elasticity in the hook structure may prevent the hook from tearing the vessel wall during withdrawal.

Figure 5:
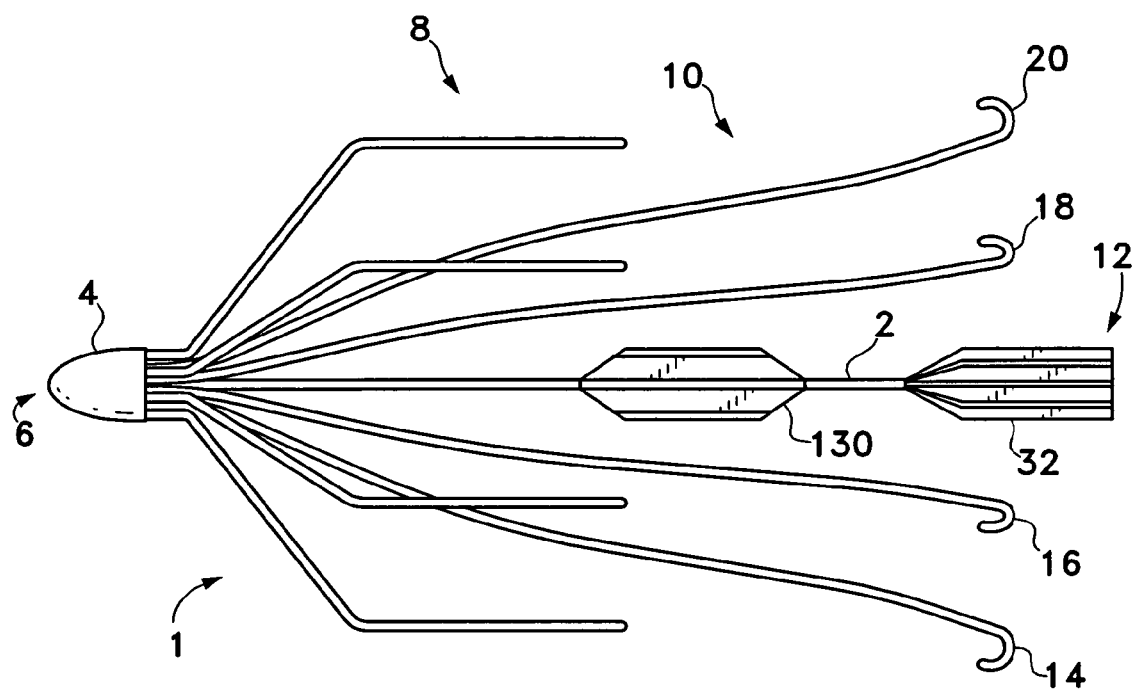
FIG. 5 illustrates another variation where two attachments are provided on the center-post for receiving the legs. In this particular variation, a first attachment is provided at the distal end to receive the hooks from the distal legs, and a second attachment is provided along mid-shaft of the center-post for receiving the proximal legs.

In another design, the vessel filter comprises two or more sets of grooves positioned along the length of the center-post for receiving the legs and/or hooks. The different sets of grooves may be provided on two or more attachments, with each attachment supporting one set of grooves. In one example, shown in FIG. 5, two attachments 32, 130 are provided along the length of the center-post 2 for receiving the legs 8, 10. A first attachment 32 is positioned at the distal end 12 of the center-post 2 for receiving the hooks 14, 16, 18, 20 from the distal legs 10. The hooks 14, 16, 18, 20 may be in a curved configuration when they are placed into the grooves on the attachment. Alternatively, the hooks 14, 16, 18, 20 may be straightened before they are placed within the grooves. A second attachment 130 is positioned along the mid-section of the center-post 2 and configured to receive the proximal legs 8. In this variation, each of the legs has a corresponding groove for receiving that leg.

Although it is preferable that each groove is designed for receiving a corresponding leg, one may also design an attachment or surface profile on the center-post with a plurality of grooves that are not pre-assigned to specific legs, such that when the legs are compressed, the legs would naturally fall into one of the convenient grooves. Preferably, each of the groove is design to receive one leg/hook, so that once a groove is filled by a leg, it would prevent a second leg from entering the same groove and forcing the second leg to go into an nearby groove.

Figure 6A:
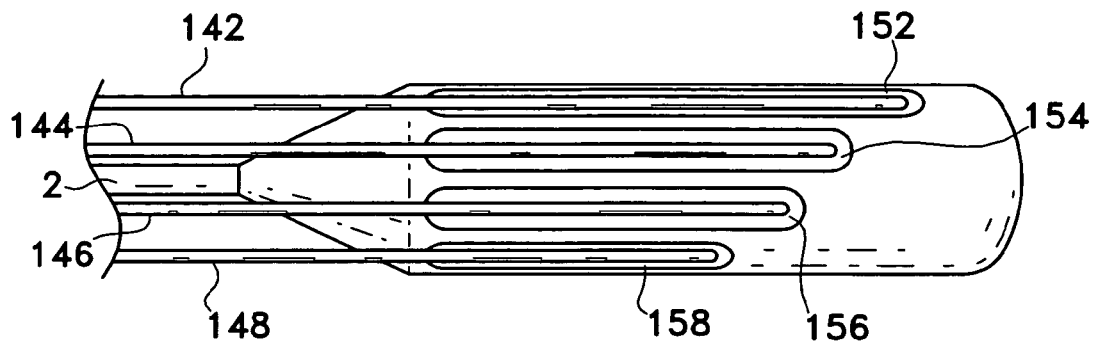
FIG. 6A illustrates another variation where the receiving slots are provided on the center-post for receiving the legs and/or hooks when the device is compressed. In this variation, the slots are configured in a step-wise manner and in a helical pattern around the circumferential surface of the center-post. The corresponding legs are also configured with varying lengths that decrease in a step-wise manner in the circumferential direction.

In yet another design, the legs of the vessel filter may have varying lengths and corresponding groves are provided on the center-post to receive the legs. In one variation, the legs 142, 144, 146, 148 with hooks are provided in a step-wise configuration forming a helical pattern along the circumferential direction around the center-post 2, as shown in FIG. 6A. Slots/grooves 152, 154, 156, 158 are provided on the center-post 2 where each of the slots has a length that matches the extension of the corresponding leg. The slots may be configured to receive the legs with their hooks in the curved position. Alternatively, the slots may be configured to receive the legs with their hooks straightened out. It is also contemplated that the slots/grooves may be configured to receive the legs with the hooks in either curved or straightened position.

Figure 6B:
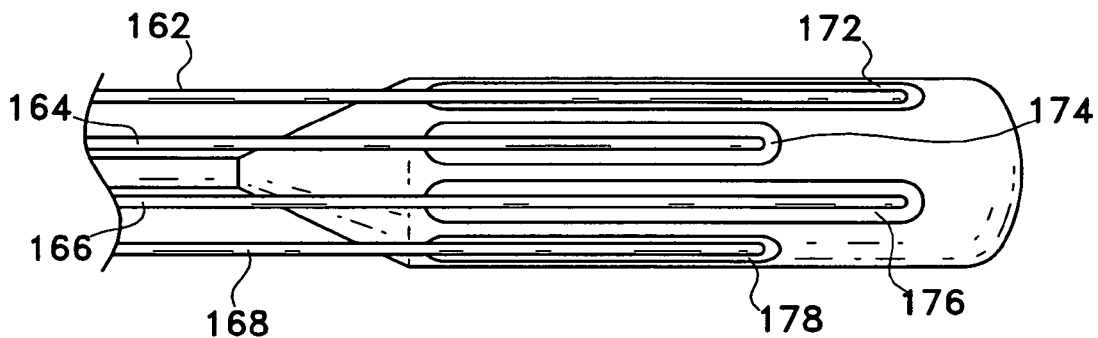
FIG. 6B illustrates yet another variation where the receiving slots are provided on the center-post for receiving the legs and/or hooks when the device is compressed. In this variation, the slots are configured in a staggered fashion and the corresponding legs comprise of legs of two different lengths forming a staggered pattern around the center-post.

In another variation, the length of the distal legs 162, 164, 166, 168 are staggered with one set of legs 162, 166 longer than the other set of legs 164, 168, as shown in FIG. 6B. In this particular configuration each of the short legs are place in between two long legs. Slots 172, 174, 176, 178 corresponding to the staggered legs are provided on the shaft of the center-post 2 for receiving the distal portion of each of the legs 162, 164, 1666, 168. As discussed earlier, depending on the particular design of the hook mechanism, the hook on each of the legs may be in a curved position or a straight position when compressed onto the center-post.

Figure 7A:
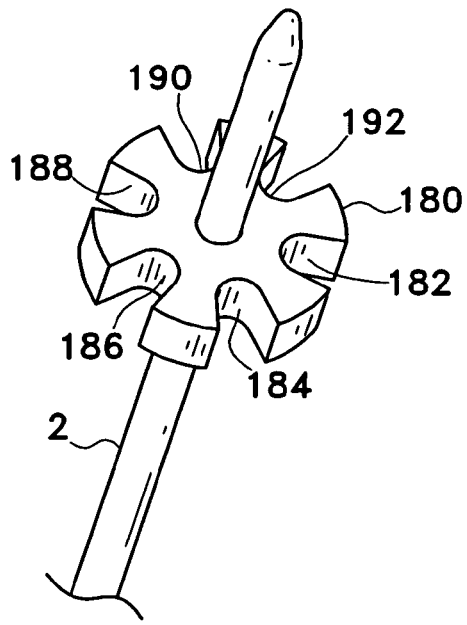
FIG. 7A illustrates another variation where the attachment for receiving the legs and/or hooks comprises a disk positioned on the center-post. The disk has slots/grooves for receiving the legs and separating the hooks from each other. The disk is shown without the corresponding legs.
Figure 7B:
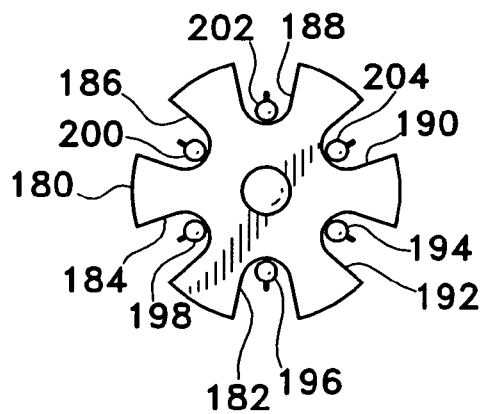
FIG. 7B shows a top view of the center-post with the disk from FIG. 7A. In this figure the disk is shown with the corresponding legs positioned within the grooves on the disk.

In another design, a disk 180 is provided on the center-post 2 for receiving the legs and/or hooks when the legs are compressed. FIG. 7A illustrates one variation where a disk 180 is positioned at the distal portion of the center-post 2. The periphery of the disk is configured with grooves/slots 182, 184, 186, 188, 190, 192 for receiving the legs of the vessel filter when the legs are compressed toward the center-post 2. In the variation shown in FIG. 7A, one disk 180 is provided at the distal portion of the center-post 2, and the center-post 2 protrude from the disk 180 and extends distally, as shown in FIG. 7A. Alternatively, the disk may be placed at the distal end of the center-post. FIG. 7B illustrates the position of the corresponding legs 194, 196, 198, 200, 202, 204 when they are placed within the grooves 182, 184, 186, 188, 190, 192 on the disk 180. The center-post may be configured with one, two or more disk. In another variation, two disks are provided along the length of the center-post. A disk is provided at the distal portion of the center-post for receiving the distal legs by capturing each of the legs at its distal portion or distal end. A second disk is provided at the mid-shaft, and it is configured with one set of grooves for receiving the distal legs (capturing each leg at its mid-section), and a second set of grooves for receiving the proximal legs.

The implantable vessel filter disclosed herein may be inserted in various vessels throughout the human body. Two common applications are (1) insertion through the right or left femoral artery for placement within the inferior vena cava, and (2) insertion into the jugular vein at the neck, also for placement at the inferior vena cava. In one example, the implantable vessel filter is prepared by collapsing the legs of the filter onto the center-post and making sure that the each of the hooks are aligned with its corresponding grooves/cavities on the center-post. The compressed vessel filter is then placed into a delivery assembly with the filter hooks close to the distal opening of the delivery assembly (i.e., the distal end of the vessel filter aligned towards distal end of the delivery assembly). The surgeon first locates a suitable jugular or subclavian vein. An incision is made to access the vein. A guide-wire is inserted into the vein and advanced towards the inferior vena cava. An introducer sheath together with its tapered dilator is advanced over the guide-wire, and the distal portion of the introducer sheath is advanced into the inferior vena cava. The guide-wire and the dilator are then removed leaving the introducer sheath with its tip in the inferior vena cava. Venacavavogram or other imaging techniques may be used to position the introducer sheath for optimal placement of the vessel filter. The delivery assembly loaded with the vessel filter is then inserted into the introducer sheath and advanced towards the inferior vena cava. Once the delivery assembly in positioned for desired placement of the vessel filter, the surgeon may then pull back on the introducer hub to retract both the introducer sheath and the delivery assembly. The pusher pad inside of the delivery assembly will force the vessel filter to exit the delivery assembly and release the filter's legs. The delivery assembly and the introducer sheath may then be removed.

In another example, the vessel filter is inserted through the femoral artery. A guide-wire is inserted through the femoral artery and advanced toward the inferior vena cava. Once the guide-wire is in place, an introducer catheter together with its tapered dilator is inserted over the guide-wire. The introducer catheter is advanced toward the inferior vena cava and positioned just below the renal veins. The guide-wire and the dilator are then removed, leaving the introducer catheter with its distal tip in the inferior vena cava. A filter storage tube, which holds the vessel filter with its legs compressed on the center-post grooves, is then attached directly to the proximal end of the introducer catheter. A pusher wire is then used to push the vessel filter into the introducer catheter with the proximal end of the vessel filter in the forward advancing direction and the pusher wire pushing on the distal end of the vessel filter. The surgeon may then continuously advance the filter toward the distal end of the introducer catheter by pushing and forwarding the pusher wire. Once the proximal end of the filter reaches the distal end of the introducer catheter, the surgeon may stop the advancement of the filter. Holding the pusher wire stationary, the surgeon may then withdraw the introducer catheter and release the vessel filter allowing the legs of the filter to expand radially. The introducer catheter and the pusher wire are then withdrawn from the patient's body.

To remove the deployed filter, one may insert an introducer catheter, with the assistance of a guide-wire and a tapered dilator, into the jugular vein and advance the introducer catheter down to the position of the deployed vessel filter. A recovery cone is inserted into the introducer catheter and advanced towards the distal end of the introducer catheter by moving a pusher shaft forward into the introducer catheter. Once the recover cone reaches the distal end of the introducer catheter, the introducer catheter is unsheathed to open the recovery cone. The recovery cone is then advanced forward and over the filter tip by advancing the pusher shaft. One may then close the recovery cone over the filter tip by advancing the introducer catheter over the cone while holding the pusher shaft stationary. The closing of the recovery cone forces the legs of the vessel filter to collapsed onto the shaft of the center-post while forcing the hooks on each of the legs into their corresponding grooves on the shaft of the center-post. The vessel filter is then drawn into the lumen of the introducer catheter, and the introducer catheter along with the vessel filter is then withdrawn from the body of the patient.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. An implantable vessel filter comprising:
   an elongated body having a proximal end and a distal end, the proximal end coupled to a hub; and
   a plurality of elongated appendages having a proximal end coupled to the hub and configured to extend radially outward from the elongated body in a filter expanded configuration, the appendages configured to collapse against the elongated body in a filter compressed configuration, some or all of the appendages including a vessel engaging hook on a distal end thereof, the elongated body including a grooved distal section configured to receive the distal ends of the appendages in the filter compressed configuration.

2. The implantable vessel filter according to claim 1, wherein the grooved distal section comprises a plurality of flanges extending radially outward from the distal section and a plurality of slots between the flanges.

3. The implantable vessel filter according to claim 2, wherein said flanges are evenly spaced around a circumferential surface of said elongated body.

4. The implantable vessel filter according to claim 1, wherein said plurality of elongated appendages comprise a set of legs each including a vessel engaging hook on a distal end thereof, the grooved distal section comprising a plurality of flanges extending radially outward from the distal section and a plurality of slots between the flanges configured to receive the distal ends of the set of legs.

5. The implantable vessel filter according to claim 4, wherein the material of each of said elongated appendages comprises a compressible spring metal.

6. The implantable vessel filter according to claim 4, wherein the material of each of said elongated appendages comprises a shape memory metal.

7. The implantable vessel filter according to claim 6, wherein said shape memory metal comprises Nitinol.

8. The implantable vessel filter according to claim 4, wherein said hooks are configured to engage and penetrate said inner wall of the vessel in an expanded position of said filter, each of said hooks being formed with a maximum migration resistance force such that a proximal withdrawal force applied to said hooks that is in excess of said filter maximum migration resistance force will cause said hooks to straighten and bend toward the filter longitudinal axis.

9. The implantable vessel filter according to claim 4, wherein said set of legs comprises six legs, and wherein the distal section includes six flanges configured to separate said hooks in the filter compressed configuration, the flanges spaced approximately equidistant from each other.

10. The implantable vessel filter according to claim 1, wherein said elongated body extends proximally beyond an interconnection between said elongated body and said plurality of elongated appendages.

11. The implantable vessel filter according to claim 10, further comprising a hook connected to the proximal end of said elongated body.

12. The implantable vessel filter according to claim 1, wherein the distal end of said elongated body extends beyond the distal ends of said plurality of elongated appendages in the filter compressed configuration.

13. The implantable vessel filter according to claim 12, the distal section including an extended section configured to facilitate handling of the filter.

14. The implantable vessel filter according to claim 12, further comprising a hook positioned at the distal end of said elongated body.

15. In a removable blood clot filter having a plurality of appendages coupled at a proximal end thereof to a hub and including vessel engaging hooks at a distal end thereof, the improvement comprising:
   a center-post coupled proximally to the hub and including a grooved distal section configured to receive said distal ends of the appendages in a compressed position.

16. The improvement according to claim 15, wherein the grooved distal section comprises a plurality of flanges extending radially outward from the center-post and a plurality of slots between the flanges.

17. The improvement according to claim 15, wherein said plurality of appendages are made from a material comprising compressible spring metal.

18. The improvement according to claim 15, wherein said plurality of appendages are made from a material comprising shape memory metal.

19. The improvement according to claim 15, further comprising a disk positioned on said center-post, wherein said disk comprises slots on the circumference of said disk for receiving said appendages.

20. The improvement according to claim 15, wherein said plurality of appendages comprise appendages of varying lengths, and wherein said grooved distal section includes grooves with varying lengths corresponding to the lengths of said appendages.

21. The improvement according to claim 15, wherein said grooved distal section includes grooves arranged in a staggered pattern around the circumference of said center-post.

22. The improvement according to claim 15, wherein said grooved distal section includes grooves arranged in a stepwise fashion along the circumferential direction around the center-post.

23. The improvement according to claim 15, wherein said grooved distal section comprises a plurality of attachments positioned on said center-post, each of said attachments including a plurality of cavities configured to receive said appendages.

* * * * *